US011752345B2

(12) United States Patent
Amsler et al.

(10) Patent No.: US 11,752,345 B2
(45) Date of Patent: Sep. 12, 2023

(54) WEARABLE MEDICAL DEVICE CONTROLLER WITH CAPACITOR FRAMING

(71) Applicant: ZOLL Medical Corporation, Chelmsford, MA (US)

(72) Inventors: Phillip Amsler, Cheswick, PA (US); Nathan J Berry Ann, Cranberry Township, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 60 days.

(21) Appl. No.: 16/949,467

(22) Filed: Oct. 30, 2020

(65) Prior Publication Data

US 2021/0128912 A1    May 6, 2021

Related U.S. Application Data

(60) Provisional application No. 62/929,721, filed on Nov. 1, 2019.

(51) Int. Cl.
| | |
|---|---|
| *A61N 1/365* | (2006.01) |
| *A61N 1/04* | (2006.01) |
| *A61N 1/362* | (2006.01) |
| *A61N 1/02* | (2006.01) |
| *A61B 5/282* | (2021.01) |
| *A61B 5/349* | (2021.01) |
| *A61B 5/00* | (2006.01) |

(52) U.S. Cl.
CPC ............. *A61N 1/365* (2013.01); *A61B 5/282* (2021.01); *A61B 5/349* (2021.01); *A61N 1/025* (2013.01); *A61N 1/0476* (2013.01); *A61N 1/3625* (2013.01); *A61B 5/6831* (2013.01)

(58) Field of Classification Search
CPC ................................. A61N 1/365; A61B 5/349
USPC .......................................................... 607/17
See application file for complete search history.

(56) References Cited

U.S. PATENT DOCUMENTS

| | | | |
|---|---|---|---|
| 4,928,690 A | 5/1990 | Heilman et al. | |
| 6,173,203 B1 | 1/2001 | Barkley et al. | |
| 6,665,191 B2 | 12/2003 | Blood et al. | |
| 10,155,118 B2 * | 12/2018 | Kaib ................... | H01M 50/20 |
| 10,269,452 B2 | 4/2019 | Volpe | |
| 10,493,289 B2 | 12/2019 | Volpe et al. | |
| 10,578,677 B2 * | 3/2020 | Kaib ................... | A61N 1/3925 |
| 2003/0004547 A1 | 1/2003 | Owen et al. | |

(Continued)

*Primary Examiner* — Nicole F Lavert
(74) *Attorney, Agent, or Firm* — THE WEBB LAW FIRM

(57) ABSTRACT

A serviceable wearable cardiac treatment device for continuous extended use by an ambulatory patient includes a garment, a device controller, and an ingress-protective housing. The garment is configured to dispose therein a plurality of ECG sensing and therapy electrodes to monitor for and treat a cardiac arrhythmia in the patient. The device controller is configured to be in separable electrical communication with the plurality of ECG sensing and therapy electrodes and includes an impact-resistant energy core, and first and second circuit boards affixed to opposing sides of the impact-resistant energy core. The impact-resistant energy core includes a frame and at least one capacitor permanently bonded to the frame to form a unitary mass. The ingress-protective housing is configured to enable removal of the impact-resistant energy core and the first and second circuit boards during servicing.

26 Claims, 21 Drawing Sheets

(56) References Cited

U.S. PATENT DOCUMENTS

| | | | |
|---|---|---|---|
| 2005/0043769 A1* | 2/2005 | Gramse | A61N 1/375 |
| | | | 607/36 |
| 2007/0213776 A1 | 9/2007 | Brink | |
| 2015/0035654 A1* | 2/2015 | Kaib | H01M 50/20 |
| | | | 340/10.51 |
| 2015/0039042 A1 | 2/2015 | Amsler et al. | |
| 2019/0255341 A1 | 8/2019 | Buchanan et al. | |

* cited by examiner

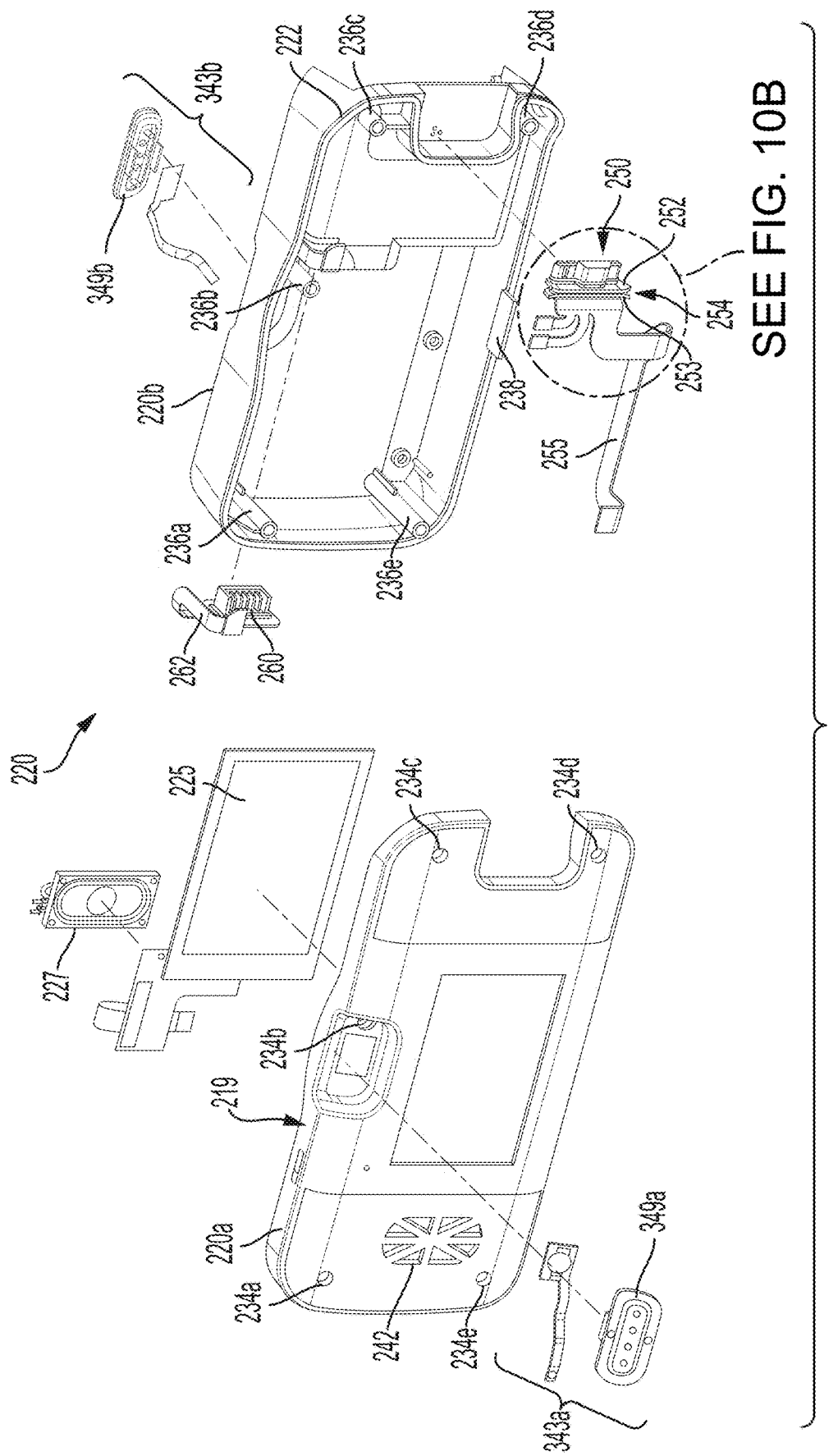

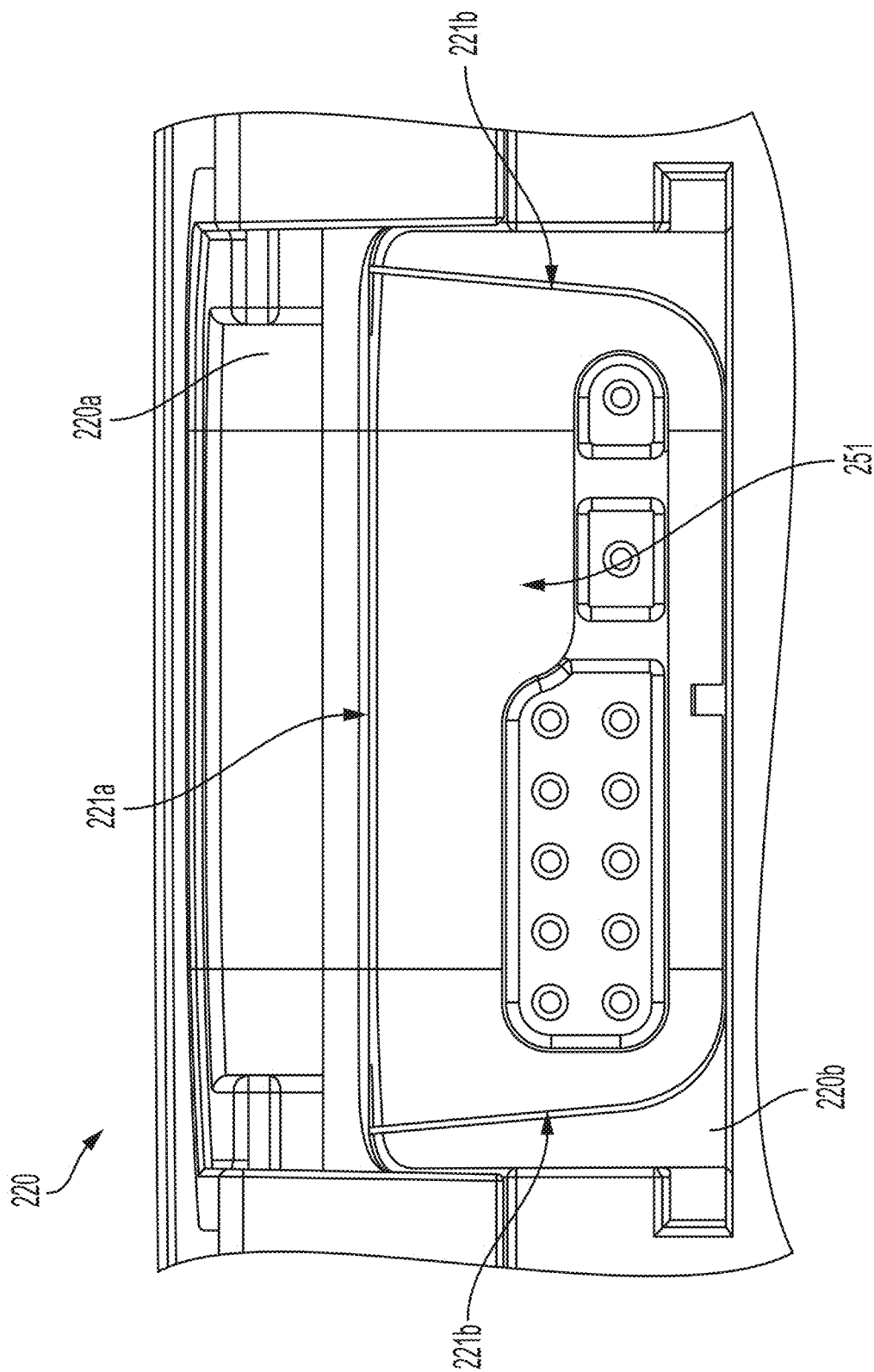

WEARABLE MEDICAL DEVICE CONTROLLER WITH CAPACITOR FRAMING

RELATED APPLICATION

This application claims the benefit of U.S. Provisional Application Ser. No. 62/929,721, titled "WEARABLE MEDICAL DEVICE CONTROLLER WITH CAPACITOR FRAMING," filed on Nov. 1, 2019. All subject matter set forth in the above referenced application is hereby incorporated by reference in its entirety into the present application as if fully set forth herein.

BACKGROUND

The present disclosure is directed to wearable cardiac monitoring and treatment devices.

A patient suffering from heart failure experiences symptoms caused by a weak or damaged heart contracting inefficiently and failing to pump effectively to circulate oxygenated blood through the body. A heart may be weakened by, for example, abnormal heart rhythms (e.g., heart arrhythmias), high blood pressure, coronary artery disease, myocardial infarction, and myocarditis.

Left untreated, heart failure could lead certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia.

Cardiac arrest can occur when various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for supporting life. It is generally useful to monitor heart failure patients in order to assess heart failure symptoms early and provide interventional therapies as soon as possible.

Wearable cardiac monitoring and treatment devices are provided to monitor for such arrhythmias and provide a treatment when a life-threatening arrhythmia is detected. Such devices are worn by the patient continuously to provide constant protection. These devices are often refurbished and reused by subsequent patients. As such, the devices need to be designed to be resilient and easy to service.

SUMMARY

In one example, a serviceable wearable cardiac treatment device for continuous extended use by an ambulatory patient includes a garment and a device controller. The garment is configured to dispose therein a plurality of ECG sensing and therapy electrodes in continuous extended contact with the patient to monitor for and treat a cardiac arrhythmia in the patient. The device controller is configured to be in separable electrical communication with the plurality of ECG sensing and therapy electrodes in the garment. The device controller includes an impact-resistant energy core and an ingress-protective housing. The impact-resistant energy core includes a frame, at least one capacitor and first and second circuit boards affixed to opposing sides of the energy core. The at least one capacitor is permanently bonded to the frame such that the frame along with the bonded at least one capacitor is a unitary mass. The at least one capacitor configured to hold electrical charge sufficient to treat the cardiac arrhythmia. The first and second circuit boards include cardiac arrhythmia monitoring and therapy circuitry in electrical communication with the at least one capacitor. The first and second circuit boards are affixed to opposing sides of the impact-resistant energy core in a manner to allow for separation from the impact-resistant energy core during service. The ingress-protective housing is configured to enable removal of the impact-resistant energy core and the first and second circuit boards during service.

Implementations of the device may include one or more of the following features.

In examples, the frame includes a pocket configured to receive the at least one capacitor therein. The device can include a compound disposed within the pocket to at least partially encapsulate the at least one capacitor thereby immovably binding the at least one capacitor to the frame to form the unitary mass. In examples, the compound includes an insulating material encasing the at least one capacitor within the pocket. The compound can include an epoxy resin that when set after initial application has a hardness rating in a range of about 80-85 Shore D. In implementations, the compound is an adhesive compound.

In examples, the at least one capacitor includes a film capacitor. In examples, the at least one capacitor includes at least two capacitors.

In examples, the device includes at least one wire extending from the impact-resistant energy core. In examples, the at least one capacitor includes two capacitors connected in parallel and the at least one wire is connected to the first circuit board. In examples, the two capacitors are two film capacitors arranged side-by-side each comprising two major planes such that the two major planes of each of the two film capacitors are disposed adjacent a first side and a second side of the frame.

In examples, the at least one capacitor is configured to occupy at least 50 to 95 percent of a volume defined within a pocket in the frame.

In examples, the device includes a gap between the at least one capacitor and an inner surface of the frame, the gap being between 0.5 to 10 mm.

In examples, the device includes one or more releasable fasteners configured to affix the first and second circuit boards to opposing sides of the impact-resistant energy core. The one or more releasable fasteners can include one or more of screws, clamps, snaps, clips, and tape.

In examples, the first circuit board includes at least one processor and high voltage circuitry in communication with the at least one processor. The at least one processor can include an arrhythmia detection processor. The at least one processor includes an arrhythmia detection processor and a therapy control processor. The high voltage circuitry can include a therapy delivery circuit.

In examples, the device includes a flex connector extending from the first circuit board to the second circuit board. The second circuit board can include low voltage circuitry, and the low voltage circuitry includes communication circuitry. In examples, the first circuit board includes a display mount configured to retain a display screen in wired communication with the second circuit board.

In examples, the impact-resistant energy core and the affixed first and second circuit boards occupy between about 25%-90% of a volume defined by the ingress-protective housing.

In examples, the ingress-protective housing includes a rear shell configured to be disposed adjacent the second circuit board and a front shell configured to be disposed adjacent the first circuit board, the front shell mating with the rear shell in a sealed configuration. In implementations, the ingress-protective housing has an IP67 or IP66 rating as set forth in the IEC 60529 Standard for Ingress Protection. In implementations, the ingress-protective housing has a rating of at least one of IP6X, IPX6, and IPX7, wherein the "X" is a variable representing a rating on a scale of 1 through 9 as set forth in the IEC 60529 Standard for Ingress Protection. A mating edge of the front shell and a mating edge of the rear shell are configured to engage in a fitted interlock when the front and rear shells are mated to form the ingress-protective housing. In implementations, at least one of the front and rear shells includes a mortise in the mating edge and the other of the front and rear sells includes a projection configured to engage the mortise. The fitted interlock can include a compressible silicone seal configured to be disposed in the mortise.

In examples, the front and rear shells are configured to be held in the sealed configuration by one or more releasable fasteners. The device can include one or more plates configured to be secured over the one or more releasable fasteners to prevent ingress of liquid and particulate matter.

In examples, the front shell and the rear shell are configured to be separated for removal and replacement of at least the impact-resistant energy core and the affixed first and second circuit boards. In implementations, the front shell can include a touch screen disposed therein, and the touch screen can be affixed to the front shell via an ingress-protective sealant. In implementations, the front shell includes a speaker disposed therein, and the speaker is sealed with an ingress-protective sealant.

In examples of the device, the separable electrical communication includes a connector in communication with the plurality of ECG sensing and therapy electrodes. The connector configured to be mated to the ingress-protective housing in electrical communication with one or both of the first and second circuit boards. In examples, the ingress-protective housing includes a receiving port for the connector, and the receiving port being in electrical communication with one or both of the first and second circuit boards. In implementations, the receiving port includes a grommet configured to receive mating edges of the front and rear shells in the sealed configuration of the ingress-protective housing. The grommet includes an upper flange and a lower flange and a well therebetween to receive the mating edges of the front and rear shells therein.

In examples, the rear shell further includes a battery connector extending therethrough configured to receive a complimentary connector of a removable battery. In implementations, the battery connector is sealed with an ingress-protective sealant and is configured to be in wired communication with at least one processor disposed on the first circuit board. The ingress-protective sealant is at least one of epoxy and pressure sensitive adhesive. The device can further include a flex connector extending between the battery connector and the first circuit board within the ingress-protective housing.

In examples, the rear shell defines a compartment configured to receive a removable battery module such that outer surfaces of the removable battery module are flush with outer surfaces of the ingress-protective housing in a mated configuration.

In examples, the rear shell further includes at least at least one shock absorbing spacer configured to protect the impact-resistant energy core and the affixed first and second circuit boards from mechanical impact. In implementations, the front shell further includes at least at least one shock absorbing spacer configured to protect the impact-resistant energy core, and the affixed first and second circuit boards from mechanical impact.

In examples, the device further includes at least one shock absorbing spacer disposed within the ingress-protective housing. The at least one shock absorbing spacer configured to support the impact-resistant energy core and the affixed first and second circuit boards within the ingress-protective housing.

In examples, the plurality of ECG sensing electrodes are configured to sense an ECG signal of the patient for further analysis by at least one processor disposed on the first circuit board.

In implementations, a method of constructing a serviceable wearable cardiac treatment device controller for continuous extended use by an ambulatory patient includes providing a frame and inserting at least one capacitor into the frame. The at least one capacitor can be configured to hold electrical charge sufficient to treat a cardiac arrhythmia of a patient. The method includes bonding the at least one capacitor to the frame such that the frame along with the bonded at least one capacitor comprises an impact-resistant energy core. The method includes affixing first and second circuit boards to opposing sides of the impact-resistant energy core in a manner to allow for separation from the impact-resistant energy core during service, the first and second circuit boards comprising cardiac arrhythmia monitoring and therapy circuitry in electrical communication with the at least one capacitor, and enclosing the energy core and the affixed first and second circuit boards within an ingress-protective housing configured to enable removal of the impact-resistant energy core and the first and second circuit boards during service.

Implementations of the method may include one or more of the following features.

In implementations, the frame includes a pocket for receiving therein the at least one capacitor therein. Bonding the at least one capacitor to the frame includes disposing a self-curing polymer within the pocket to at least partially encapsulate the at least one capacitor and thereby immovably bind the at least one capacitor to the frame to form a unitary mass.

The ingress-protective housing can include a rear shell configured to be disposed adjacent the second circuit board and a front shell configured to be disposed adjacent the first circuit board. In implementations of the method of constructing the serviceable wearable cardiac treatment device controller includes enclosing the energy core and the affixed first and second circuit boards within an ingress-protective housing by mating a front shell with the rear shell in a sealed configuration. The method can include securing the front and rear shells in their sealed configuration with one or more releasable fasteners.

Mating the front and rear shell can include engaging a mating edge of the front shell and a mating edge of the rear shell in a fitted interlock to form the ingress-protective housing. In implementations, mating the front and rear shells includes engaging a mortise disposed on a mating edge of one of the front and rear shells with a projection disposed on a mating edge of the other of the one of the front and rear shells. The method can further include disposing a compressible silicone seal in the mortise.

BRIEF DESCRIPTION OF THE DRAWINGS

FIG. 10A depicts an exploded view of an example enclosure for a device controller for a wearable cardiac monitoring and treatment device.

FIG. 13 depicts a portion of a side view of an example assembled device controller for a wearable cardiac monitoring and treatment device.

DETAILED DESCRIPTION

Figure 1:
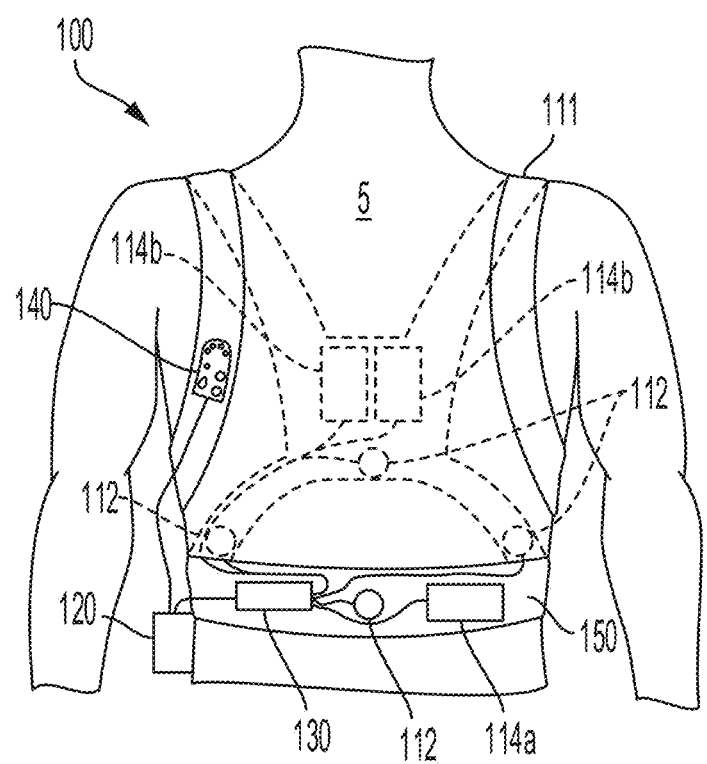
FIG. 1 depicts a schematic front view of an example wearable cardiac monitoring and treatment device including a device controller.

Heart failure patients can be prescribed a cardiac monitoring device or a cardiac monitoring and treatment device. In some cases, physicians may use medical devices alone or in combination with drug therapies to treat heart failure conditions. Depending on the underlying condition being monitored or treated, medical devices such as cardiac monitors or defibrillators may be surgically implanted or externally connected to the patient. In some examples, the cardiac monitoring device may be an external wearable cardiac device for ambulatory use. Wearable medical devices, such as cardiac event monitoring devices, are used in clinical or outpatient settings to monitor and record various physiological signals for a patient. In some examples, a wearable cardiac monitoring and treatment device may be a wearable defibrillator configured to monitor for cardiac arrhythmias and provide a treatment when a life-threatening arrhythmia is detected. Such a device can be worn by the patient continuously to provide constant protection and subsequently can be refurbished for reuse by another patient. Systems and techniques disclosed herein improve the resiliency and serviceability of a device controller for a wearable cardiac monitoring and treatment device.

This disclosure relates to a patient-worn cardiac monitoring and treatment device that detects one or more treatable arrhythmias based on physiological signals from a patient. The treatable arrhythmias include those that may be treated by defibrillation pulses, such as ventricular fibrillation (VF) and shockable ventricular tachycardia (VT), or by pacing pulses, such as bradycardia, tachycardia, and asystole. A wearable medical device as disclosed herein monitors a patient's physiological conditions, e.g., cardiac signals, respiratory parameters, and patient activity, and delivers potentially life-saving treatment to the patient. The medical device can include a plurality of sensing electrodes that are disposed at various locations on the patient's body and configured to monitor the cardiac signals of the patient, such as electrocardiogram (ECG) signals. In some implementations, the device can also be configured to allow a patient to report his/her symptoms including one or more skipped beat(s), shortness of breath, light headedness, racing heart, fatigue, fainting, and chest discomfort. The device determines an appropriate treatment for the patient based on the detected cardiac signals and/or other physiological parameters prior to delivering a therapy to the patient. The device then causes one or more therapeutic shocks, for example, defibrillating and/or pacing shocks, to be delivered to the body of the patient. The wearable medical device includes a plurality of therapy electrodes disposed on the patient's body and configured to deliver the therapeutic shocks.

In implementations, a garment portion of the wearable cardiac monitoring and treatment device is configured to be worn or otherwise secured about the torso of the patient. A plurality of energy storage units are operably connected to a therapy delivery circuit. The energy storage units are configured to store energy for at least one therapeutic pulse. The therapy delivery circuit is configured to cause the delivery of the at least one therapeutic pulse via the plurality of therapy electrodes. In implementations, the energy storage units are electrically coupled by one or more cables to the plurality of therapy electrodes. For example, the one or more cables are electrically insulated and physically isolated from the skin of the patient and other components of the device when the garment is assembled along with the plurality of energy storage units, therapy delivery circuit, and therapy electrodes.

In some implementations, the wearable cardiac monitoring and treatment device includes sensors configured to detect one or more physiological signals of the patient. Such physiological sensors may include at least one physiological sensor configured to monitor signals indicative of cardiac activity, such as ECG signals and/or heart rate of the patient. For example, such ECG sensors can include one or more ECG electrodes configured to be in contact with the patient. The ECG electrodes can be placed in contact with the patient's skin, for example, on the torso of the patient. In some examples, the one or more ECG electrodes are a plurality of ECG sensors in contact with a torso of the patient and configured to monitor an ECG signal of the patient.

The devices described here are prescribed to be worn continuously and for long durations of time, often over the course of several weeks or months. For example, a prescribed duration can be a duration for which a patient is instructed by a caregiver to wear the device in compliance with device use instructions. A device designed for an extended duration of wear may be prescribed for some or all of the designed duration as described subsequently. A sudden cardiac arrest or other arrhythmia condition can strike at any time and with little warning. Patients are encouraged to comply with the device use guidelines, including wearing the device at all times including while showering or sleeping. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. In some implementations, the patient may remove the wearable medical device for a short portion of the day (e.g., for half an hour to bathe). The devices, therefore, are configured to withstand impact from environmental factors and forces associated with daily continuous use by an ambulatory patient. Additionally, the devices are configured to allow for uncomplicated assembly and disassembly during servicing for repair and/or refurbishing for reuse by subsequent patients.

Further, the wearable medical device can be configured as a long term or extended use medical device. Such devices can be configured to be used by the patient for an extended period of 24 hours or more, several days, weeks, months, or even years. Accordingly, the extended use can be uninterrupted until a physician or other caregiver provides specific prescription to the patient to stop use of the wearable medical device. For example, the wearable medical device can be prescribed for use by a patient for an extended period of at least one week. In an example, the wearable medical device can be prescribed for use by a patient for an extended period of at least 30 days. In an example, the wearable medical device can be prescribed for use by a patient for an extended period of at least one month. In an example, the wearable medical device can be prescribed for use by a patient for an extended period of at least two months. In an example, the wearable medical device can be prescribed for use by a patient for an extended period of at least three months. In an example, the wearable medical device can be prescribed for use by a patient for an extended period of at least six months. In an example, the wearable medical device can be prescribed for use by a patient for an extended period of at least one year.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, for example, analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator previously described.

Regardless of the extended period of wear, the use of the wearable medical device can include continuous or nearly continuous wear by the patient as described above. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, heart vibrations, etc.) and/or non-cardiac information (e.g., blood oxygen, the patient's temperature, glucose levels, tissue fluid levels, and/or lung vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

FIG. 1 illustrates an example medical device 100 that is external, ambulatory, and wearable by a patient, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time for which the patient wears the wearable defibrillator, the wearable defibrillator can be configured to continuously or substantially continuously monitor the vital signs of the patient and, upon determination that treatment is required, can deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 111, one or more sensing electrodes 112 (e.g., ECG electrodes), one or more therapy electrodes 114a and 114b (collectively referred to as therapy electrodes 114), a medical device controller 120, a connection pod 130, a patient interface pod 140, a belt 150, or any combination of these. In some examples, at least some of the components of the medical device 100 can be configured to be affixed to the garment 111 (or in some examples, permanently integrated into the garment 111), which can be worn about the patient's torso 5.

The medical device controller 120 (e.g., the controller 120) can be operatively coupled to the sensing electrodes 112, which can be affixed to the garment 111, e.g., assembled into the garment 111 or removably attached to the garment, e.g., using hook and loop fasteners. In some implementations, the sensing electrodes 112 can be permanently integrated into the garment 111. The controller 120 can be operatively coupled to the therapy electrodes 114. For example, the therapy electrodes 114 can also be assembled into the garment 111, or, in some implementations, the therapy electrodes 114 can be permanently integrated into the garment 111. The controller 120 contains hardware and electronics to monitor and treat the patient. In implementations, the controller 120 can be serviced and/or refurbished for subsequent use by another patient. Implementations of the controller 120 described herein, therefore, include one or more features directed toward facilitating uncomplicated and successful disassembly and reassembly without compromising the ingress-protective assembly of the controller 120.

Component configurations other than those shown in FIG. 1 are possible. For example, the sensing electrodes 112 can be configured to be attached at various positions about the body of the patient. The sensing electrodes 112 can be operatively coupled to the controller 120 through the connection pod 130. In some implementations, the sensing electrodes 112 can be adhesively attached to the patient's body, such as to the torso 5. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, heart vibrations, lung vibrations, respiration vibrations, patient movement, etc. Example sensing electrodes 112 include a metal electrode with an oxide coating such as tantalum pentoxide electrodes.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the controller 120. One or more of the therapy electrodes 114 can be configured to deliver one or more therapeutic defibrillating shocks to the torso 5 of the patient when the medical device 100 determines that such treatment is warranted based on the signals detected by the sensing electrodes 112 and processed by the medical device controller 120. Example therapy electrodes 114 can include conductive metal electrodes such as stainless steel electrodes. In certain implementations, each therapy electrode 114 includes one or more conductive gel deployment devices configured to deliver conductive gel to the metal electrode prior to delivery of a therapeutic shock.

In implementations, each therapy electrode of the at least one pair of therapy electrodes 114, 114a, 114b, has a conductive surface adapted for placement adjacent the patient's skin and has an impedance reducing means, e.g. an impedance reducing conductive gel, contained therein for reducing the impedance between a therapy electrode and the patient's skin. In implementations, the patient-worn arrhythmia monitoring and treatment device 100 may include gel deployment circuitry (e.g., the gel deployment circuit 205 of FIG. 2) configured to cause the delivery of conductive gel substantially proximate to a treatment site (e.g., a surface of the patient's skin in contact with the therapy electrode 114) prior to delivering therapeutic shocks to the treatment site. As described in U.S. Pat. No. 9,008,801, titled "WEARABLE THERAPUETIC DEVICE," issued on Apr. 14, 2015 (hereinafter the "'801 patent"), which is hereby incorporated herein by reference in its entirety, the gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry, for example the gel deployment circuit 205 of FIG. 2, may be coupled to or integrated within a therapy electrode or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the garment as part of the therapy delivery systems, while the cartridges may be removable and/or replaceable.

In some implementations, the gel deployment modules may be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry may be removable and/or replaceable. In other examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Figure 2:
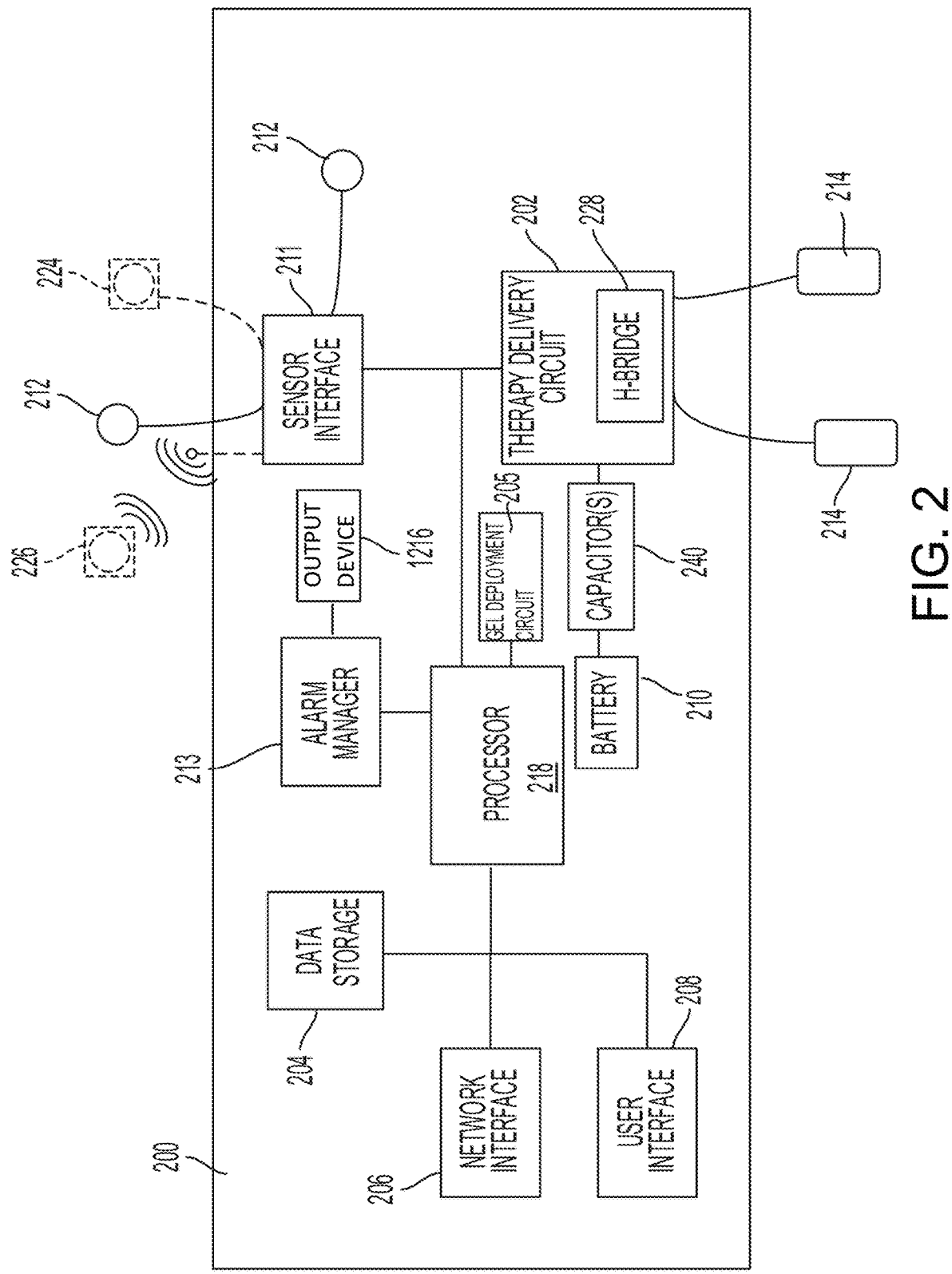
FIG. 2 depicts a schematic diagram of an embodiment of a device controller for a wearable cardiac monitoring and treatment device.

FIG. 2 illustrates a sample component-level schematic of an example medical device controller 200, which could be an implementation of the device controller 120 of FIG. 1, for example. As shown in FIG. 2, the medical device controller 200 can include a therapy delivery circuit 202 including a polarity switching component such as an H-bridge 228, a data storage 204, a network interface 206, a user interface 208, at least one battery 210, at least one capacitor 240, a sensor interface 211, an alarm manager 213, and at least one processor 218. A patient monitoring medical device can include a medical device controller 200 that includes like components as those described above, but does not include at least the therapy delivery circuit 202 and at least one capacitor 240.

The therapy delivery circuit 202 can be coupled to one or more therapy electrodes 214 configured to provide therapy to the patient (e.g., therapy electrodes 114 as described above in connection with FIG. 1). For example, the therapy delivery circuit 202 can include, or be operably connected to, circuitry components that are configured to generate and provide the therapeutic shock. The circuitry components can include, for example, resistors, one or more capacitors, relays and/or switches, an electrical bridge such as an H-bridge 228 (e.g., including a plurality of insulated gate bipolar transistors or IGBTs that deliver and truncate a therapy pulse, as described in further detail below), voltage and/or current measuring components, and other similar circuitry arranged and connected such that the circuitry work in concert with the therapy delivery circuit 202 and under control of one or more processors (e.g., processor 218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, the one or more capacitors include a parallel-connected capacitor bank consisting of one capacitor or a plurality of capacitors (e.g., two, three, four or more capacitors). These capacitors can be switched into a series connection during discharge for a defibrillation pulse. For example, four capacitors of approximately 500 μF can be used. In one implementation, the capacitors can have between 500 to 2500 volt surge rating and can be charged in approximately 5 to 30 seconds from a battery pack depending on the amount of energy to be delivered to the patient. Additional implementations of capacitor properties and arrangements on a patient-worn medical device are provided herein in subsequent sections.

In implementations, the gel deployment circuit 205 is coupled to the processor 218 and configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. The gel deployment circuit 205 may be coupled to or integrated within a therapy electrode 214 or other therapy delivery device as a single unit. When a treatable cardiac condition is detected and no patient response is received after device prompting, the gel deployment circuit 205 can be signaled to deploy the conductive gel.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 200. In certain implementations, the data storage 204 can include executable instructions that, when executed, are configured to cause the processor 218 to perform one or more functions.

In some examples, the network interface 206 can facilitate the communication of information between the medical device controller 200 and one or more other devices or entities over a communications network. For example, where the medical device controller 200 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s), e.g., a base station, a "hotspot" device, a smartphone, tablet, a portable computing device, and/or other devices in proximity of the wearable medical device. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 200. For example, the user interface 208 can include one or a combination of a screen display, a touch screen display, LED and/or LCD display, LED lights, physical buttons, soft buttons (e.g., touch fields on a screen), one or more speakers, and/or one or more microphones.

The medical device controller 200 can also include at least one battery 210 configured to provide power to one or more components integrated in the medical device controller 200. The battery 210 can include a rechargeable multi-cell battery pack. In one example implementation, the battery 210 can include three or more 2000 mAh lithium ion cells that provide electrical power to the other device components within the medical device controller 200. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 200.

The sensor interface 211 can be coupled to one or more sensors configured to monitor one or more physiological parameters of the patient. As shown, the sensors may be coupled to the medical device controller 200 via a wired or wireless connection. The sensors can include one or more electrocardiogram (ECG) sensing electrodes 212 (e.g., similar to sensing electrodes 112 as described above in connection with FIG. 1), heart vibrations sensors 224, and tissue fluid monitors 226 (e.g., based on ultra-wide band radiofrequency devices).

The ECG sensing electrodes 212 can monitor a patient's ECG information. For example, the ECG sensing electrodes 212 can include conventional stick-on adhesive electrodes, conductive electrodes with stored gel deployment, e.g., metallic electrodes with stored conductive gel configured to be dispersed in the electrode-skin interface when needed, or dry electrodes, e.g., a metallic substrate with an oxide layer in direct contact with the patient's skin. The ECG sensing electrodes 212 can be configured to measure the patient's ECG signals. The ECG sensing electrodes 212 can transmit information descriptive of the ECG signals to the sensor interface 211 for subsequent analysis.

The vibration sensors 224 can include heart vibration sensors to detect a patient's heart vibration information. For example, the vibrations sensors 224 can be configured to detect heart vibration values including any one or all of S1, S2, S3, and S4. From these heart vibration values, certain electromechanical metrics may be calculated, including any one or more of electromechanical activation time (EMAT), percentage of EMAT (% EMAT), systolic dysfunction index (SDI), and left ventricular systolic time (LVST). The vibrations sensors 224 can include an acoustic sensor configured to detect vibrations from a subject's cardiac system and provide an output signal responsive to the detected heart vibrations. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the heart vibrations information or patient position/movement to the sensor interface 211 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 211 for subsequent analysis.

The sensor interface 211 can be coupled to any one or combination of sensing electrodes/other sensors to receive other patient data indicative of patient parameters. Once data from the sensors has been received by the sensor interface 211, the data can be directed by the processor 218 to an appropriate component within the medical device controller 200. For example, if heart data is collected by heart vibrations sensor 224 and transmitted to the sensor interface 211, the sensor interface 211 can transmit the data to the processor 218 which, in turn, relays the data to a cardiac event detector. The cardiac event data can also be stored on the data storage 204.

In certain implementations, the alarm manager 213 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 213 can be implemented using hardware or a combination of hardware and software. For instance, in some examples, the alarm manager 213 can be implemented as a software component that is stored within the data storage 204 and executed by the processor 218. In this example, the instructions included in the alarm manager 213 can cause the processor 218 to configure alarm profiles and notify intended recipients using the alarm profiles. In other examples, alarm manager 213 can be an application-specific integrated circuit (ASIC) that is coupled to the processor 218 and configured to manage alarm profiles and notify intended recipients using alarms specified within the alarm profiles. Thus, examples of the alarm manager 213 are not limited to a particular hardware or software implementation.

In some implementations, the processor 218 includes one or more processors (or one or more processor cores) that each are configured to perform a series of instructions that result in manipulated data and/or control the operation of the other components of the medical device controller 200. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to a specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. The processor 218 can be configured to execute a function stored in software. For example, such software may be stored in a data store coupled to the processor 218 and configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display and audio generation, basic networking, firewalling, data encryption and communications.

In implementations, the controller 200 is configured to provide one or more high energy shocks to the torso 5 of a patient, for example up to five successive defibrillation shocks of 150 J to 500 J of energy to a patient experiencing a cardiac arrhythmia such as ventricular fibrillation or ventricular tachycardia. The controller 200 therefore includes considerations for avoiding patient exposure to high voltage components and considerations for protecting the components therein from damage due to normal usage and ingress of fluid or other contaminants during a prescribed period of continuous wear.

In implementations, a serviceable, rugged, wearable cardiac treatment device for continuous extended use by an ambulatory patient includes a garment (e.g. garment 111 of FIG. 1) configured to dispose therein a plurality of ECG sensing electrodes 212 and therapy electrodes 214 in continuous extended contact with the torso 5 of the patient to monitor for and treat a cardiac arrhythmia in the patient. The device can include an impact resistant, ingress-protected device controller (e.g. controller 120 or controller 200) configured to be in separable electrical communication with the plurality of ECG sensing electrodes 212 and therapy electrodes 214 in the garment.

Figure 3:
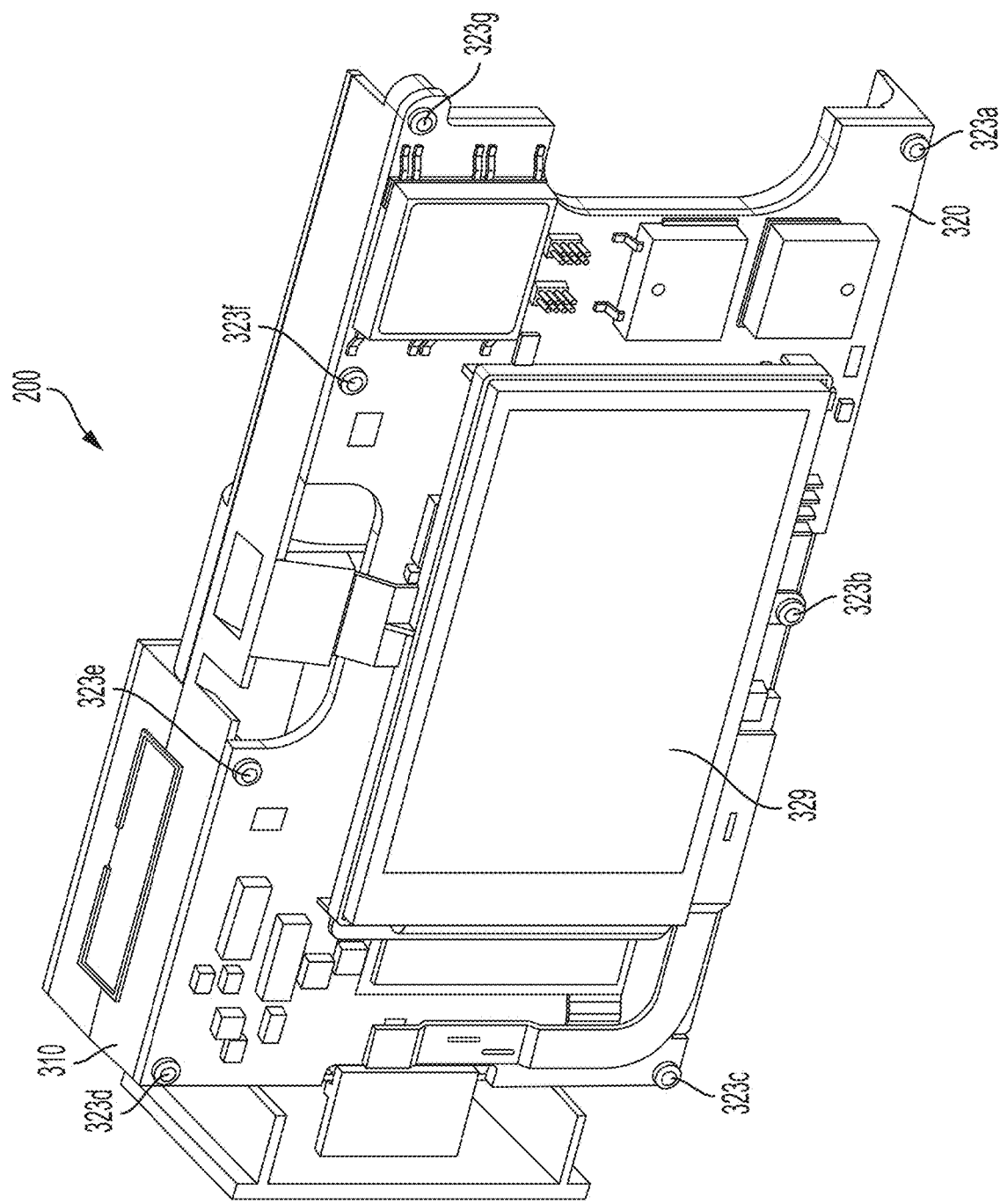
FIG. 3 depicts a front perspective view of a core assembly of an example device controller for a wearable cardiac monitoring and treatment device.
Figure 4:
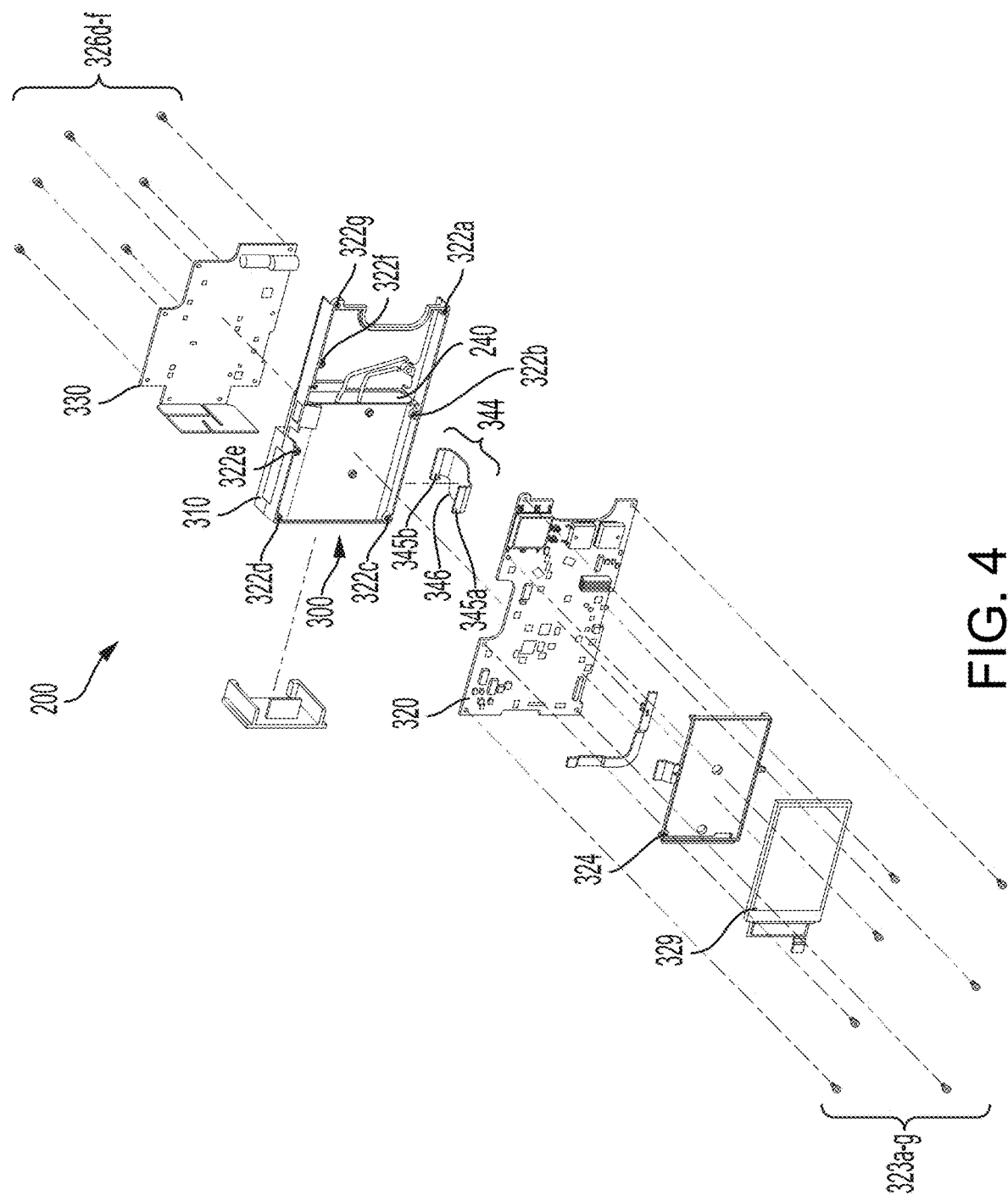
FIG. 4 depicts an exploded view of the core assembly of FIG. 3.
Figure 5:
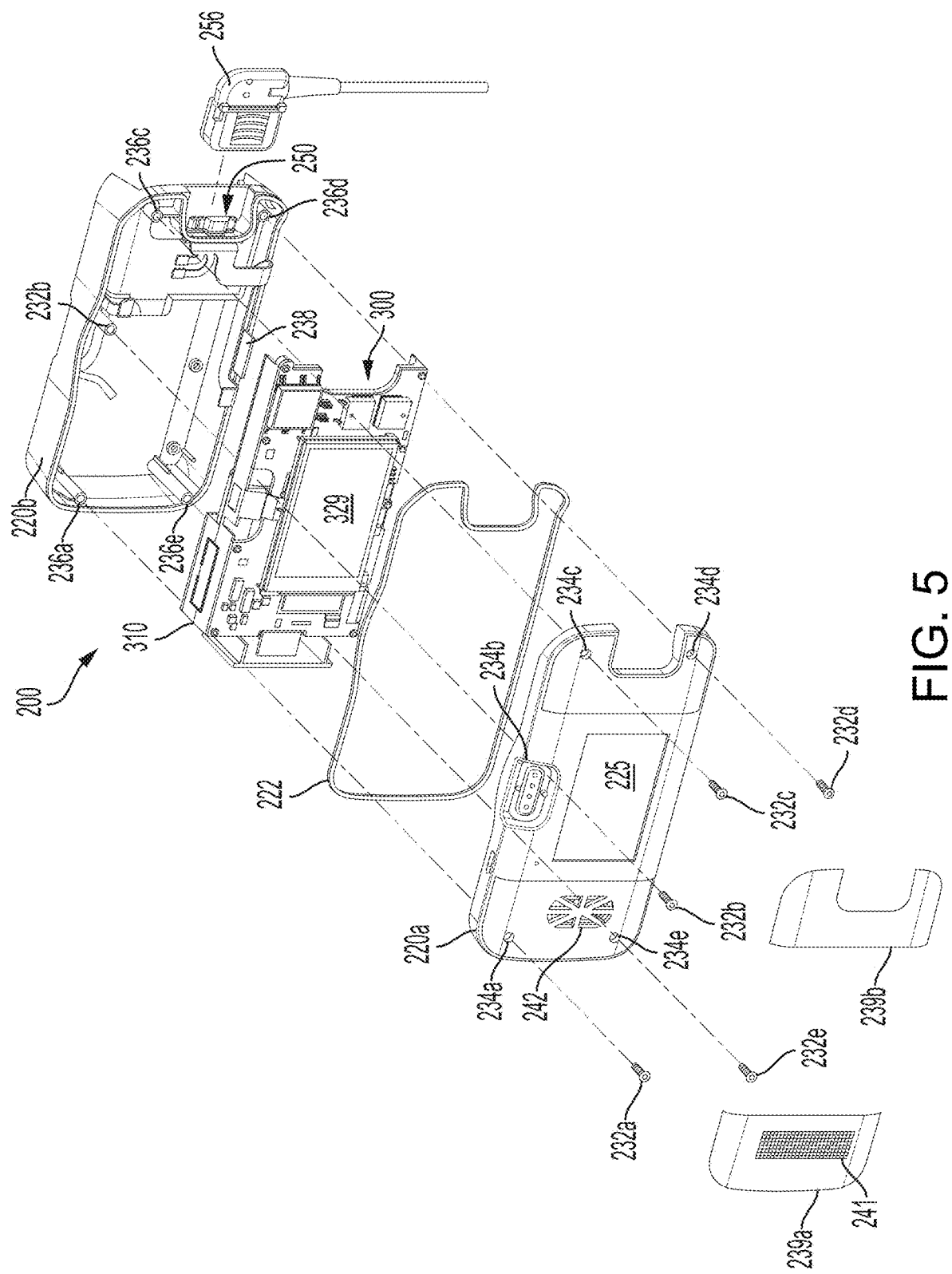
FIG. 5 depicts an exploded view of an example device controller for a wearable cardiac monitoring and treatment device.

In implementations, such as that of FIGS. 3 through 5, the device controller 200 includes an impact resistant energy core 300, a first circuit board 320, a second circuit board 330, and an ingress-protective housing 220, 220a, 220b configured to encapsulate the core 300 and the first and second circuit boards 320, 330 while still enabling removal of the impact-resistant energy core 300 and the first and second circuit boards 320, 330 during servicing. In implementations, the impact-resistant energy core 300 includes a frame 310, and a least one capacitor (e.g. capacitor 240). In implementations, the at least one capacitor (e.g. capacitor 240) is permanently bonded to the frame 310 such that the frame 310 along with the bonded at least one capacitor comprises a unitary mass.

The frame 310 can be a lightweight structure manufactured from a non-conductive material such as a plastic and/or thermoplastic that is an electrical insulator. The characteristics of the material of the frame include maximizing dielectric strength, minimizing moisture absorption and maximizing mechanical strength. For example, the frame 310 can comprise at least one of polypropylene, Polyethylene (PE), Polyvinyl chloride (PVC), acrylic, polycarbonate, ULTEM 1000, NORYL N1150, and VALOX E45329. In implementations, the frame 310 exhibits high flexural strength in accordance with ASTM D638 and ISO527 standards, a resistance to absorbing moisture in accordance with ASTM D570 and ISO 62 standards, a resistance to a wide range of bases and acids, a high resistance to fatigue in accordance with ASTM D790 and ISO178 standards and a high impact strength in accordance with ASTM D256 and ISO 180/1A standards. In implementations, the frame 310 can have a dielectric strength in a range of about 500-900 V/mil in air. In implementations the frame can have a dielectric constant at 1 kHZ, 50% RH in a range of about 2.75-3.25. In implementations, the frame can have a dissipation factor in a range of about 0.001-0.002 and a volume resistivity at $^1\!/_{16}$ of about $1.0 \times 10(^{17})$ Ohm-cm. In implementations the frame can have a moisture absorption in a range of about 0.05-0.25 percent. In implementations the frame can have a tensile strength in a range of about 7,500-16,000 psi at 23 degrees Celsius (e.g., 73 degrees Fahrenheit). In implementations the frame 310 can have a flexural yield strength in a range of about 10,000-25,000 psi. In implementations the frame 310 can have an impact strength (Izod, notched) in a range of about 1.0-2.0 ft-lb/in in accordance with the ASTM D256 standard. In implementations, the frame 310 can have a Rockwell hardness of 109 on the "M" scale in accordance with ASTM standard D785. In implementations, the frame 310 can have an ultimate shear strength in a range of about 10,000-20,000 psi. In examples, the materials noted above provide some or all of these properties. In one example the frame 310 can be made of a material having the following properties shown in Table 1:

TABLE 1

| Properties | Units | Example Value |
|---|---|---|
| Water Absorption, @Equilibrium, 73° F. (23 C.) | % | 0.25 |
| Tensile Strength, Break, 73° F. | psi | 15,000 |
| Elongation, Break, 73° F., ASTMD638 | % | 60 |
| Elongation, Yield, 73° F., ASTMD638 | % | 7-8 |
| Flexural Strength, 73° F. | psi | 22,000 |
| Flexural Modulus, 73° F. | psi | 475,000 |
| Izod Impact Strength, Notched, 73° F. | ft-lb/in | 1.0 |
| Rockwell Hardness | "M" Scale | 110 |
| Compressive Strength, ASTMD695 | psi | 21,500 |
| Compressive Modulus, ASTMD695 | psi | 475,000 |
| Shear Strength, Ultimate | psi | 15,000 |
| Dielectric Strength, In Air | V/mil | 700 |
| Dielectric Constant, 1 kHz, 50% RH | — | 3.10 |
| Dissipation Factor 1 kHz, 50% RH, 73° F. (23° C.) | — | 0.0012 |
| Volume Resistivity, $^1\!/_{16}$" | ohm-cm | $10 \times 10^{17}$ |

Figure 6A:
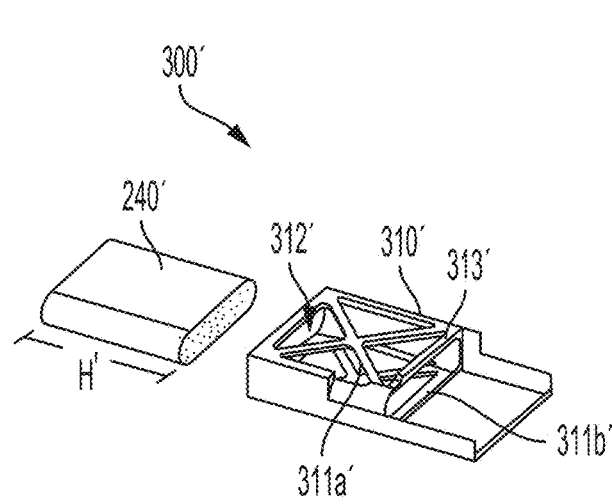
FIG. 6A depicts an exploded perspective view of an example framing assembly for a capacitor for an example device controller for a wearable cardiac monitoring and treatment device.
Figure 6B:
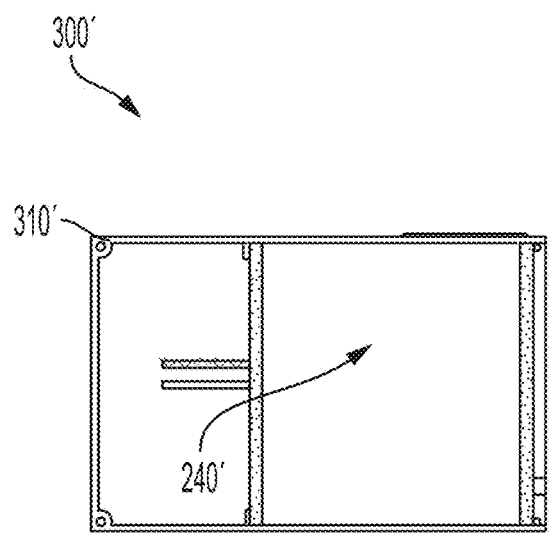
FIG. 6B depicts a plan view of the example framing assembly of FIG. 6A.
Figure 6C:
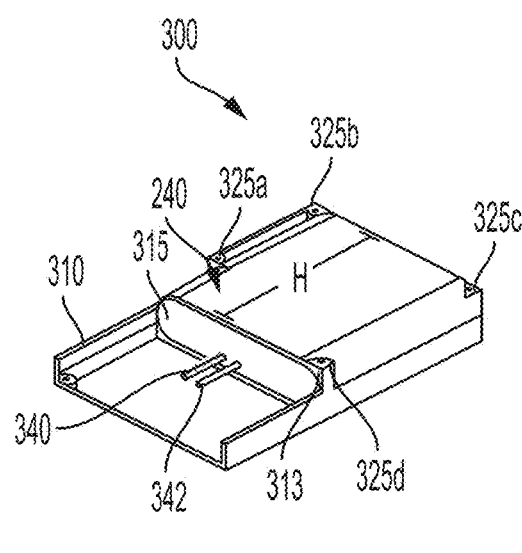
FIG. 6C depicts a perspective view of another example framing assembly for a capacitor for an example device controller for a wearable cardiac monitoring and treatment device.
Figure 6D:
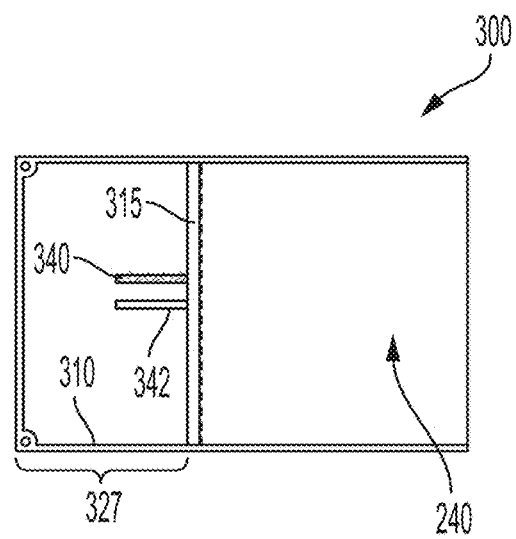
FIG. 6D depict a plan view of the example framing assembly of FIG. 6C.
Figure 7:
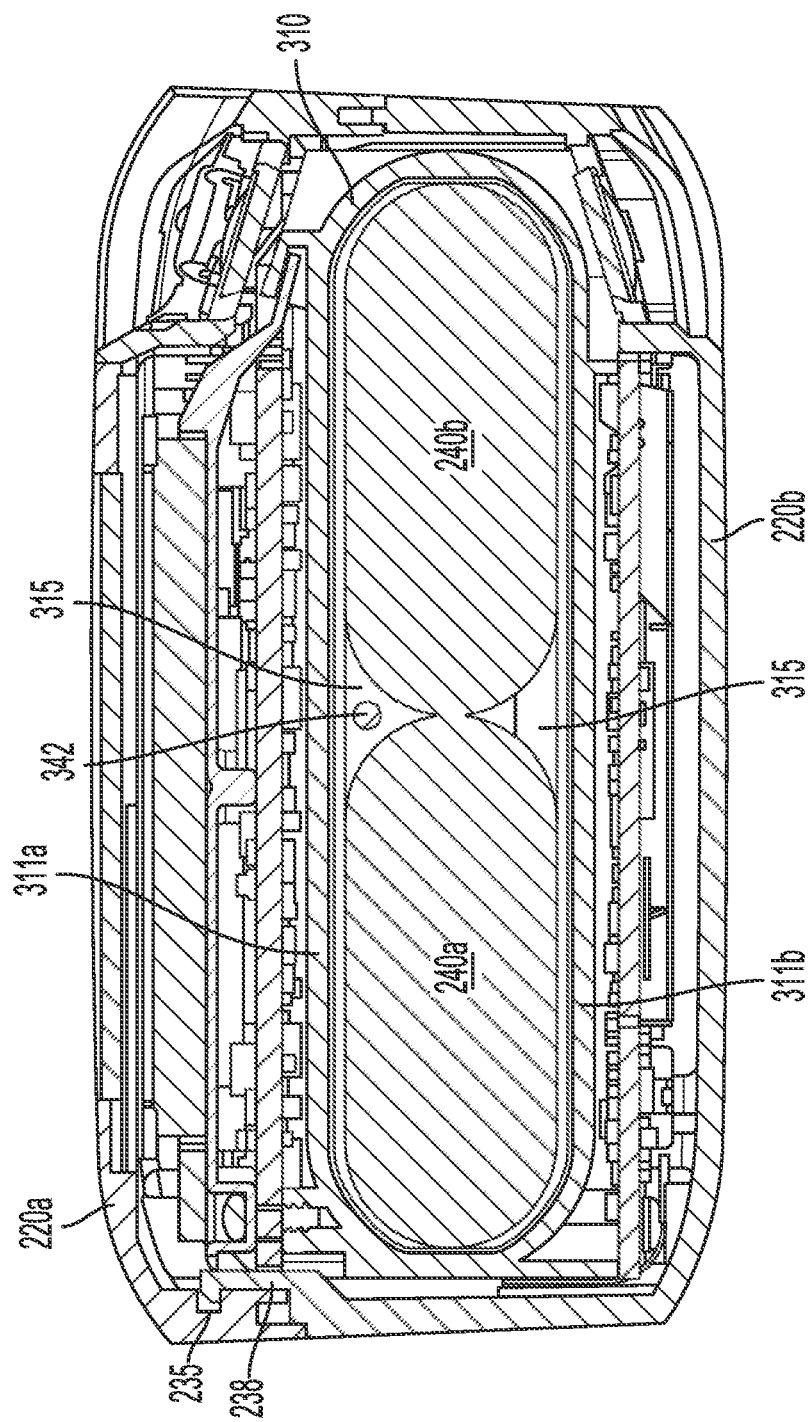
FIG. 7 depicts a side cross section of an example assembled device controller for a wearable cardiac monitoring and treatment device.

Returning to the construction of the energy core 300, in implementations, the frame 310 receives the at least one capacitor 240 therein. As shown in FIGS. 6A and 6C, for example, the frame 310, 310' can comprise a pocket or well 312, 312' sized, shaped, and/or configured to receive the at least one capacitor 240, 240' therein. In one example, as shown in FIGS. 6C through 7 the pocket 312 encapsulates the at least one capacitor 240, 240a, 240b disposed therein by having solid walls forming the pocket 312 and comprising a mouth 313 at an open end of the pocket 312 for receiving the at least one capacitor 240 therethrough. In implementations, the pocket 312 is at least as deep as the height H of the at least one capacitor 240 such that the at least one capacitor is at or below the mouth 313 of the pocket 312 when inserted. Because the frame 310 comprises a non-conductive, insulating material such as plastic, the pocket 312 isolates the high voltage at least one capacitor 240 from other components of the controller 200.

In implementations, shown in FIGS. 6C through 7, the high energy core 300 includes a compound 315 disposed within the pocket 312 to immovably bind the at least one capacitor 240 to the frame 310 to form the unitary mass. In implementations, the compound 315 is an adhesive compound. The compound 315 can at least partially encapsulate the at least one capacitor 240. In implementations, the compound 315 can include an electrically insulating material (which may be dispersed in an adhesive medium). The compound 315 can encase the at least one capacitor 240 within the pocket 312. In implementations, the compound 315 can be an epoxy resin configured to be applied to the pocket in a liquid state and that, when set after initial application, has a hardness rating of in a range of about 80-85 Shore D. In implementations, the compound 315 is a low viscosity epoxy (e.g., a viscosity of 400-700 centipoise (CPS)) that off-gasses and releases bubbles during a curing phase to release air and maintain high voltage properties of the assembly. In implementations, the compound 315 is a viscose polymer that hardens at room temperature (e.g., around 25-55F). In implementations, the compound 315 is at least one of a marine grade epoxy and a UL listed epoxy. For example, the compound 315 can be at least one of a WEST SYSTEM epoxy resin, such as 105 Epoxy Resin, by WEST MARINE of Watsonville, Calif. For example, the compound 315 can be at least one of a TAP marine grade epoxy resin, such as TAP 314 Epoxy Resin, by TAP PLASTICS, INC. of San Leandro, Calif. For example, the compound can be at least one of a UL Listed epoxy, such as UL 94 V-0 Listed Epoxy, by EPOXIES, ETC. of CRANSTON, R.I. In implementations, such materials, as noted above, include dielectric materials that absorb moisture while providing voltage isolation of the at least one capacitor 240.

In one example, the compound 315 can have a tensile strength in a range of about 8,000-12,000 PSI, a compressive strength in a range of about 20,000-24,000 PSI, and a flexural strength in a range of about 14,000-20,000 PSI. In an example, the compound 315 is characterized by resistance to cracking when exposed to impact, vibration, and thermal shock and has a tensile strength in a range of 10,000 PSI, a compressive strength of 22,000 PSI, and a flexural strength of 17,000 PSI. In implementations, the compound 315 has a dielectric strength less than or equal to 6.0 at both 1 kHz and 1 MHz, in accordance with ASTM D150. In implementations, the compound 315 has a dissipation factor, or dielectric loss, of less than or equal to 0.03 at 1 kHz and less than or equal to 0.05 at 1 MHz, in accordance with ASTM D150. In implementations, the compound 315 has a dialectic strength in a range of about 200-650 Volts/mil at about 25 degrees C., and a dielectric constant of between about 3-6 and a dissipation factor of between about 0.005-0.01 at about 25 degrees C. and 100 hz. In one example, the compound 315 has a dielectric strength of 500 volts/mil, a dielectric constant of 4.4, and a dissipation factor of 0.007 at about 25 degrees C. and 100 hz. In implementations, a volume resistivity the compound 315 is greater than or equal to 0.1 teraohm-meter at about 25 degrees C. and greater than or equal to 1.0 megaohm-meter at 125 degrees C., according to ASTM D257.

In implementations, the compound 315 can be applied at the mouth 313 of the pocket 312, across an exposed end of the at least one capacitor 240. In other implementations, the compound 315 can be applied to the bottom of the pocket 312 prior to insertion of the at least one capacitor 240. The compound 315 can be applied to the bottom of the pocket 312 before insertion of the at least one capacitor 240 and across the mouth 313 of the pocket 312 and the exposed end of the at least one capacitor, adhering to both the at least one capacitor 240 and frame 310. Once set, the compound 315 immovably binds the at least one capacitor 240 to the frame 310. As such, the at least one capacitor 240 does not move relative to the frame 310 and cannot be removed from the frame 310. In this manner, the at least one capacitor 240 and the frame 310 are assembled into a unitary mass with no moving parts once the compound 315 is hardened. The impact resistant energy core 300 therefore is a solid mass comprising the at least one capacitor 240 immovably bonded and unable to be separated from to the frame 310. In view of at least these aspects of its construction, the core 300 can be withstand impacts without damaging the high voltage components confined therein. The core 300 is resistant to impact damage and therefore designed to prevent electrical failure. By strengthening the core 300, the device 100 is able to be used by an ambulatory patient on a daily, continuous schedule during normal wear and tear activities without compromising the ability of the device 100 to monitor the patient and deliver treatment when necessary.

Although implementations of the energy core 300 described above include a frame 310 pocket 312 having continuous, unperforated, unbroken walls, other implementations can include a pocket having one or more semi-perforated or scaffolding-style walls and/or no bottom wall to reduce the overall weight of the frame 310. In the implementation of FIG. 6A, for example, the energy core 300' includes a pocket 312' having two perforated sidewalls, 311a', 311b'. In such implementations, the assembled core 300', such as that of FIG. 6B, includes additional structural elements configured to hold the at least one capacitor 240' to the frame 310' until a curable, hardening compound 315' is added to one or both ends of the pocket 312' to bind the at least one capacitor 240' to the frame 310'.

Returning to FIG. 7, a cross section view of an embodiment of the core 300 is depicted. In examples, the at least one capacitor 240 comprises a film capacitor. In examples, such as that of FIG. 7, the at least one capacitor comprises at least two capacitors 240a, 240b. The at least two capacitors 240a, 240b can be inserted into the pocket 312 in a side-by-side arrangement such that each of the two major planes of each capacitor is disposed adjacent a first sidewall 311a and second sidewall 311b of the frame 310. In implementations, the at least two capacitors are shorted together at both ends, the top and bottom ends, such that they are electrically in parallel and effectively act as one capacitor in the circuitry of the controller 200. In examples, each of the at least two capacitors 240a, 240b are flattened film capacitors with a maximum thickness of between 1 mm and 40 mm, a capacitance of at least 50 microfarads, and a breakdown voltage rating between 1300 and 2500 volts. In an example, the at least two capacitors 240a, 240b are each an 81.25 µf film capacitor (e.g., about 162.5 µf combined capacitance) and have a combined surge rating of about 1600V.

In examples, the at least two capacitors 240a, 240b are shorted together at their aligned ends with a conductive plate, and the energy core 300 includes at least one wire extending from the at least two capacitors 240a, 240b beyond the pocket 312 of the frame 310. The at least two capacitors 240a, 240b can be connected in parallel, and the at least one wire can be connected to the first circuit board 320 to communicate with the at least one processor 218 and the therapy delivery circuit 202. In implementations, the at least one wire includes two wires 340, 342, as shown in FIGS. 6C-D and 19A-B.

Figure 19A:
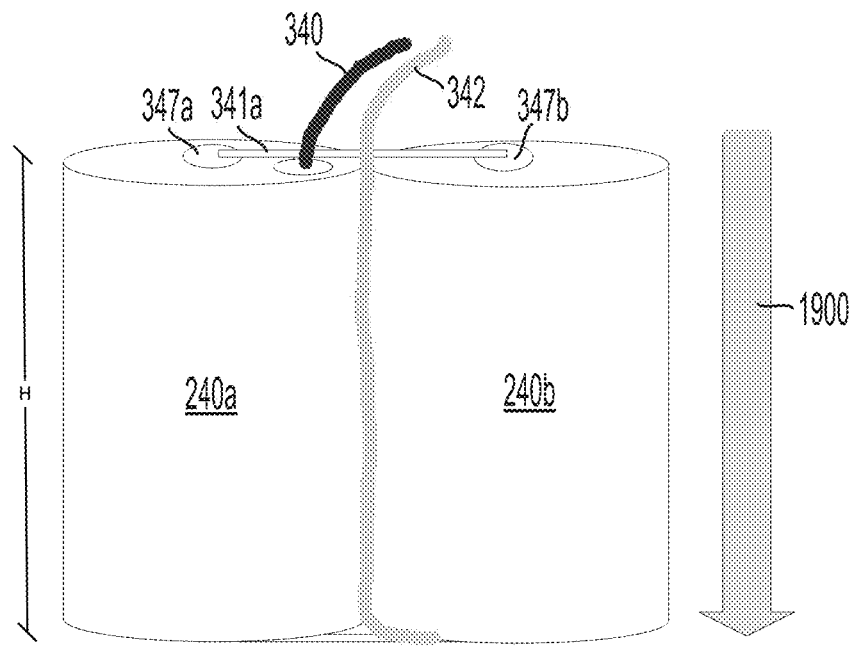
FIG. 19A depicts a view of an example capacitor assembly for device controller for a wearable cardiac monitoring and treatment device.
Figure 19B:
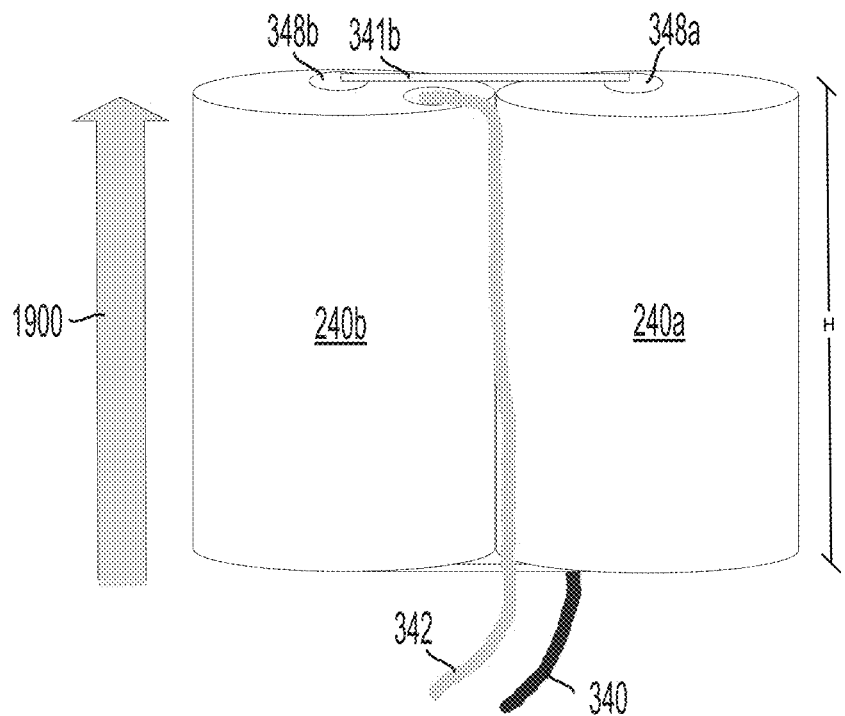
FIG. 19B depicts a rotated view of the example capacitor assembly of FIG. 19A

FIGS. 19A-B depict top and bottom views of an embodiment of two capacitors 240a, 240b connected in parallel by first and second connectors 341a, 341b, such as conductive metal plates, electrically coupled at each end to each of the two capacitors 240a, 240b. The ends of the first and second connectors 341a, 341b can be attached to the two capacitors 240a, 240b with conductive solder 347a-b, 348a-b applied at top and bottom ends of each of the two capacitors 240a, 240b such that the first and second connectors adhere to and bridge across the top and bottom surfaces of the two capacitors 240a, 240b. A first wire 340 of the can be electrically connected to a top end of the at least one capacitor (e.g., the at least two capacitors 240a, 240b) and a second wire 342 can be electrically connected to a bottom end of the at least one capacitor. Although the adjectives "top" and "bottom" are applied here in one configuration, the terminology could be applied in the alternative. The example of FIGS. 19A and 19B further include an arrow 1900 indicating the direction of insertion of the two electrically coupled capacitors 240a, 240b into a pocket 312 of a frame 310. In this example, the top end of the electrically coupled capacitors 240a, 240b is closest to the mouth 313 of the pocket 312 when the energy core 300 is fully assembled.

Because the second wire 342 is connected to the bottom end of the electrically coupled capacitors 240a, 240b, the second wire 342 is at least as long as the height H of the coupled capacitors 240a, 240b. For example, as shown in FIG. 7, the second wire 342 is connected to the shorted ends of the at least two capacitors 240a, 240b at the bottom of the pocket and threaded up the pocket 312, along and between the at least two capacitors, toward the mouth 313 of the pocket 312. As shown in FIG. 6D, the first wire 340 connected to the shorted ends of the at least two capacitors at the mouth 313 of the pocket 312 extends from the pocket 312 adjacent the second wire 342. The first and second wires 340, 342 can be prevented from disconnecting from the at least two capacitors by the compound which flows around the first and second wires 340, 342 when added to the energy core 300 and then hardens to immovably bind the wires 340, 342 to the unitary mass of the energy core 300. The first and second wires 340, 342 are configured to be electrically coupled to the first circuit board 320 affixed to the energy core 300.

In implementations, the at least one capacitor 240 occupies at least 50 to 95 percent of a volume defined by the pocket 312 of the frame 310. In some examples, the at least one capacitor 240 touches one or more walls 311 of the pocket 312 and is electrically insulated by the high dielectric frame 310. In other examples, a gap of between 0.5 to 10 mm between one or more portions of the inner surface of the pocket 312 and the at least one capacitor 240 disposed therein is configured to receive the compound 315 such that the compound extends along the height H of the at least one capacitor between the at least one capacitor and the inner surface of the pocket 312. In implementations, such as that of FIG. 7, the compound flows around the second wire 342 that extends from the bottom of the at least one capacitor up through the pocket 312 to the mouth 313 and hardens over time to secure the second wire 342 in this configuration within the pocket 312.

The impact resistant energy core 300 therefore is a unitary mass of at least one capacitor 240 bound to the frame 310 by a compound, such as a self-curing polymer, that immobilizes the at least one capacitor and the at least one wire electrically connected to the at least one capacitor. Additional components of the controller 200 are formed around the high energy core 300, which provides a central, stable, solid, unbendable, and impact resistant foundation upon which to affix additional hardware.

As described previously with regard to FIGS. 3 through 5, the controller 200 includes a first circuit board 320 and a second circuit board 330. Although the first circuit board 320 and second circuit board 330 are described herein as "first" and "second," these terms are purely illustrative for describing implementations of characteristics and features associated with each of two circuit boards. The terms "first" and "second" could be applied in the alternative to each of the other board. In implementations, the first circuit board 320 and the second circuit board 330 include cardiac arrhythmia monitoring and therapy circuitry in electrical communication with the at least one capacitor 240. The first circuit board 320 and second circuit board 330 can be affixed to opposing sides of the impact-resistant energy core 300 in a manner to allow for separation from the impact-resistant energy core 300 during servicing. In implementations, one or more releasable fasteners affix the first and second circuit boards 320, 330 to opposing sides of the impact-resistant energy core 300. For example, the one or more releasable fasteners can include one or more of screws, clamps, snaps, clips, and tape.

In examples, such as that of FIGS. 3 and 4, the first and second circuit boards 320, 330 are affixed to the frame 310 with one or more removable screws. For example the first circuit board 320 is configured to be affixed to the frame 310 with a plurality of screws 323a-g configured to be inserted through receiving holes disposed about the perimeter of the first circuit board 320 and securely threaded into receiving threads of screw bosses 322a-g disposed about the perimeter of the frame. Similarly the second circuit board 330 is configured to be affixed to the frame with a plurality of screws 326a-f configured to be inserted through receiving holes disposed about the perimeter of the first circuit board and securely threaded into receiving threads of screw bosses disposed about the perimeter of the frame, for example the screw bosses 325a-d of FIG. 6C. Although the implementation described herein includes screws that can be inserted and tightened and loosened and removed repeatedly, implementations of the controller 200 can include other releasable fasteners for retaining the first and second circuit boards 320, 330 on opposing sides of the energy core 300. For example, four spring loaded, press-fit retention clips can engage each of the four sides of both major faces of the core and each of the first and second circuit boards 320, 330 can be pressed into the retention clips so that one of the two largest planar surfaces of each of the first and second circuit boards 320, 330 is face-to-face with one of the two largest planar surfaces of the energy core 300. In other implementations, double sided adhesive tape can be used to fasten each of the first and second circuit boards 320, 330 to opposing sides of the core 300. In some implementations, multiple modes of fastening (e.g., screws and adhesive tape, or screws and epoxy material) may be used to secure either or both of the first and second circuit boards 320, 330.

In implementations, the first circuit board 320 and second circuit board 330 are configured to be disposed on opposing sides of the energy core 300. The opposing sides are the largest planar surfaces of the energy core 300. In implementations the first and second circuit boards 320, 330 each have two largest planar surfaces, one of each configured to be disposed face-to-face on one of the opposing sides of the energy core 300 such that the assembly of the energy core 300 and first and second circuit boards 320, 330 is compact. In implementations, 50-100% of a periphery of each of the first and second circuit boards 320, 330 contacts the energy core 300. In implementations, the first and second circuit boards 320, 330 are configured to be in electrical communication via a flexible connector 344 (FIG. 4) extending from the first circuit board 320 to the second circuit board 330. The flexible connector 344 can releasably connect to the first and second circuit boards 320, 330 via a releasable connector 345a, 345b at each end and includes a flexible, flat ribbon cable 346 therebetween that wraps around an outer edge of the frame 310.

In implementations the first and second circuit boards 320, 330 overlap the pocket 312 of the energy core 300 and the at least one capacitor 240 therein. In implementations, such as those shown in FIGS. 8 and 9, the frame 310 can include an overhang portion 327 extending beyond the mouth 313 of the pocket 312 such that the entire length of the first circuit board 320 is disposed on the entire length of the frame 310. In implementations, the second circuit board 330 is shorter than the first circuit board 320 and does not extend over the overhang portion 327. The overhang portion can include a sidewall neck down 328a, 328b such that a side wall of the overhang portion is shorter than a sidewall of the pocket. The overhang portion 327 therefore is configured to receive therein a battery well, or compartment, formed in the rear shell 220b of the ingress-protective housing 220. The well and rear housing will be described subsequently with regard to implementations of the ingress-protective housing 220.

Returning to FIGS. 8 and 9, in implementations, the first circuit board 320 includes hardware and circuitry supporting critical monitoring and treatment functions and the second circuit board 330 includes hardware and circuitry supporting non-critical functions that can be suspended or updated, for example, without disturbing the critical monitoring and treatment functions of the first circuit board 320. In examples, the first circuit board 320 comprises at least one processor (e.g., processor 218) and high voltage circuitry (e.g., the therapy delivery circuit 202) in communication with the at least one processor. In implementations, the at least one processor includes an arrhythmia detection processor. In implementations the at least one processor includes an arrhythmia detection processor and a therapy delivery circuit 202. The first circuit board 320 can include thereon a speaker for communicating alerts and critical notifications and instructions to a patient or caregiver, a health indicator LED, and at least one user response button 343, 343a, 343b with which a patient communicates directly with the one or more processors on the first circuit board 320. For example, the patient can press and release the at least one user response button 343, 343a, 343b to indicate consciousness and delay a treatment in response to a notification of imminent shock. The at least one user response button can be two response buttons 343a, 343b, located on the top of the housing 220, on opposite sides of the housing. In implementations the two opposed response buttons 343a, 343b can be located at a central spot along the top of the controller 200. Such a construction can allow a patient to quickly reach down and place fingers on the response buttons without having to remember which end of the housing 220 includes the at least one response button.

Figure 14B:
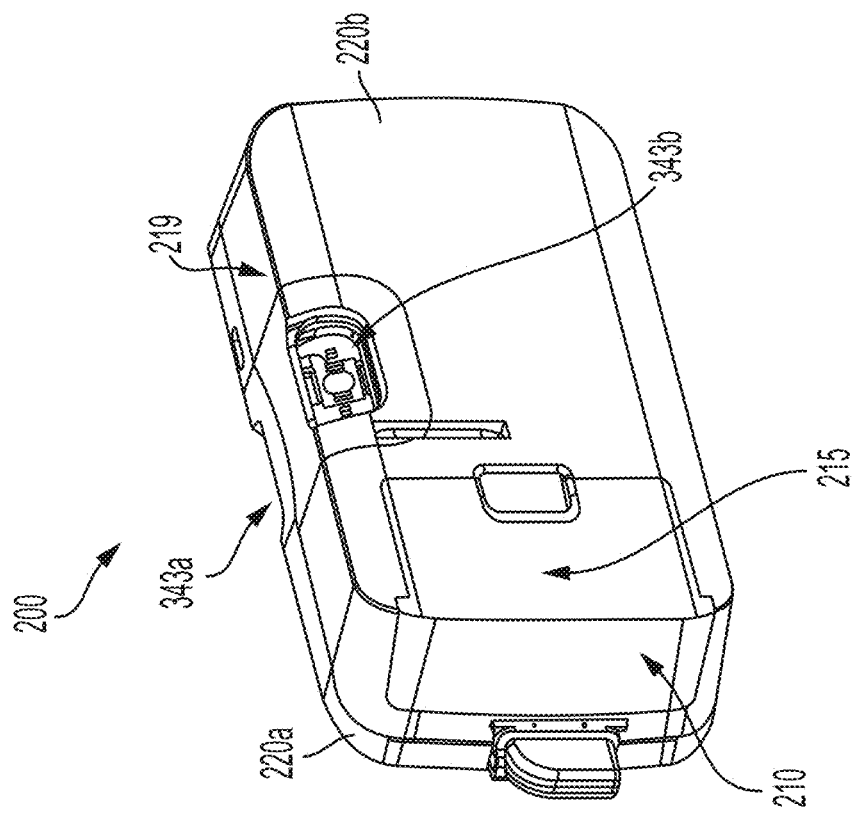
FIG. 14B depicts a rear perspective view of the example assembled device controller of FIG. 14A with the battery inserted.
Figure 14A:
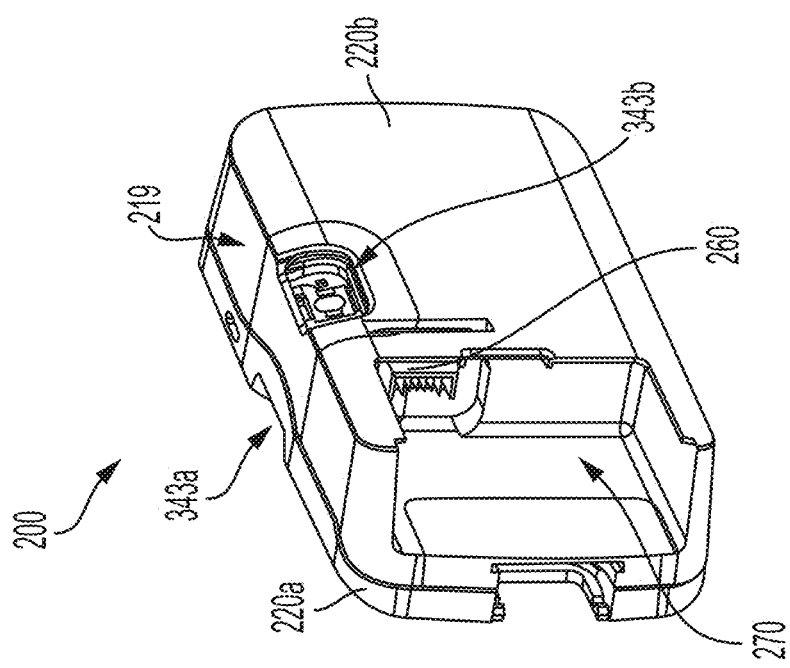
FIG. 14A depicts a rear perspective view of an example assembled device controller for a wearable cardiac monitoring and treatment device with the battery removed.

For example, as best shown in FIGS. 10A and 14A-B, the position of the at least one response button, e.g., two response buttons 343a, 343b, is centrally located at a top edge 219 of each of the front and rear shells 220a, 220b. In addition to their central location, the two response buttons 343a, 343b can be recessed within the front and rear shells 220a, 220b such that a patient can quickly locate the response buttons and center their fingers upon the buttons for proper alignment and application of force. The top edge 219 of the front and rear shells can be notched and beveled to further facility efficient and accurate location of the response buttons. Additionally, as shown best in FIG. 10A, the two response buttons 343a, 343b can be covered with an overmold 349a, 349b, such as at least one of rubber, silicone, and a urethane thermoplastic. The overmold can include textured elements, such as one or more of raised nubs and ridges easily felt with a pad of a finger. When the controller 200 provides a warning of imminent shock, an alert patient attempting to delay treatment may be startled and/or worried about quickly providing a response that delays treatment. By placing the buttons along an easily located edge of the housing 220, by recessing them, and by covering them with a patterned overmold, a patient can easily use the sense of touch to quickly discern the buttons 343a, 343a from the material of the front and rear shells 220a, 220b and align their finger with the button for an effective application of force.

In some implementations, alternatively or in addition, a patient can provide a response to an alert of an arrhythmia detection by touching a field on the display 329. In an example, upon detecting a cardiac arrhythmia, the processor 218 of the device can output to the display 329 an alert and/or notification. The alert and/or notification can include one or more capacitive fields configured to receive a touch input or a pattern of touches from a responsive patient requesting a delay in treatment. In implementations, the processor 218 may require a sequence of touches to verify that the patient is intentionally requesting a delay of treatment rather than accidentally touching a button on the display 329.

While the first circuit board 320 includes the at least one processor 218 for controlling alerts, treatment, and user interactions with the display 329 and/or response buttons 343a, 343b in implementations, the second circuit board 330 includes low voltage circuitry, including at least one of communication circuitry (e.g., Cellular, WiFi, NFC), display and touch screen drivers, and one or more supercapacitors to drive a shutdown of applications running on one or more processors of the second circuit board 330. In implementations, such as that of FIG. 8, the first circuit board 320 includes a display mount 324 for receiving and retaining a display screen 329. In implementations the display screen 329 is in wired communication with the second circuit board 330 and the display and touch screen drivers. In implementations, the second circuit board 330 includes the network interface 206. The network interface can include communications circuitry for transmitting data in accordance with a BLUETOOTH wireless standard for exchanging such data over short distances to an intermediary device(s) (e.g., a base station, a "hotspot" device, a smartphone, a tablet, a portable computing device, and/or other devices in proximity of the wearable medical device 100). In implementations, the network interface can communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the network interface can communicate with a remote server over a WI-FI communications link based on the IEEE 802.11 standard.

Figure 9:
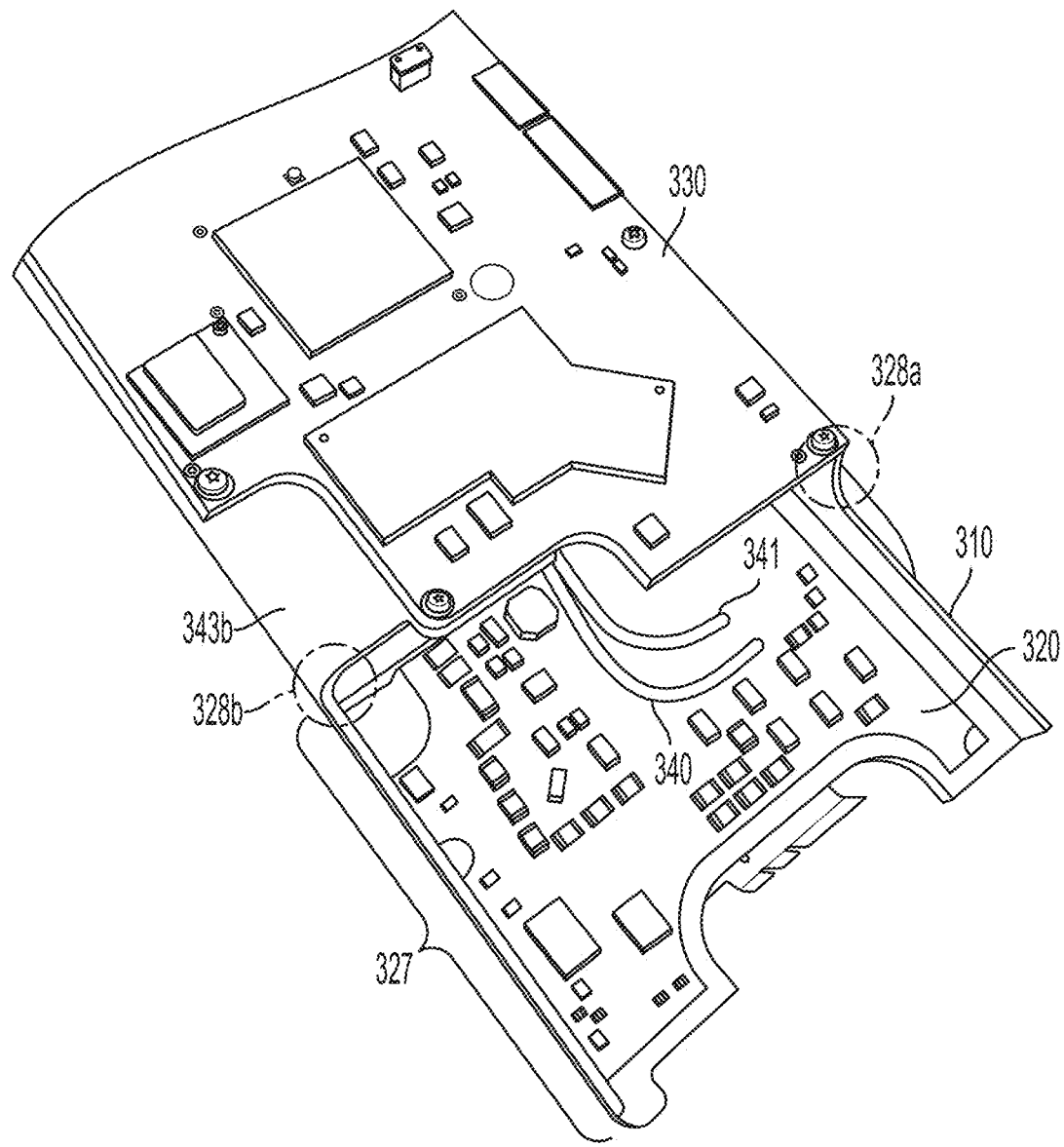
FIG. 9 depicts a rear perspective view of the internal assembly of FIG. 8.

As described above with regard to implementations, the first circuit board 320 and second circuit board 330 and their associated hardware and circuitry components are assembled around the energy core 300. The energy core 300 and the at least one capacitor 240 therein, therefore, form the core of the assembly of the controller 200, and the at least one capacitor 240 is in electrical communication with the first circuit board 320 and second circuit board 330 via at least one wire. As shown in FIG. 9, in implementations, the at least one wire, e.g., first and second wires 340, 342, is in electrical communication with the first circuit board 320 such that the at least one capacitor 240 is in communication with the at least one processor 218 and the high voltage circuitry (e.g., therapy delivery circuit 202). In implementations, the at least one wire, e.g., first and second wires 340, 342, is soldered to a corresponding at least one contact, via, or through hole on the first circuit board 320. As depicted in FIG. 9, the first and second circuit boards 320, 330 are affixed to opposing sides of the unitary mass of the energy core and the at least one wire, e.g., first and second wires 340, 342, extends from the energy core and is configured to attach to the first circuit board 320 within the confines of the frame 310. If the assembly of the energy core 300 and first and second circuit boards 320, 330 is jostled during routine daily activities of the patient wearing the device 100, the at least one wire is not under any tension or torque and does not pull away from or separate from the first circuit board 320. The at least one wire is therefore protected by being immobilized relative to the frame 310 and the first circuit board 320.

In embodiments of other devices, free standing electrolytic capacitors can be mounted at one end to a circuit board. For example, a capacitor bank could include four freestanding electrolytic capacitors individually soldered to a circuit board such that four individual leads are secured. If one of the freestanding electrolytic capacitors dislodges and disconnects from the circuit board in response to impact, the entire capacitor bank would fail to provide sufficient energy for delivering a therapeutic shock.

In contrast, the energy core 300 is the unitary mass at the core of the assembly of the controller 200. The controller 200 is formed around the at least one capacitor 240, for example two capacitors electrically connected in parallel. This reduces the number of wires requiring connection to a circuit board and reduces the points of failure. Additionally, in implementations of the at least one capacitor 240 including two capacitors connected in parallel and bound to the dielectric frame 310 by a compound, the two capacitors are immobilized relative to one another. Unlike freestanding capacitors, the at least one capacitor (e.g., the two capacitors 240a, 240b of FIG. 7) are part of the unitary mass of the energy core 300 and withstand impact associated with daily activities of the patient and with being accidentally dropped, for example. The energy core 300 and at least one capacitor 240 retained therein withstand the force of such impact without moving relative to one another and without moving relative to the first and second circuit boards 320, 330 affixed to the energy core 300.

In addition to including a rugged, impact-resistant energy core 300, the device 100 includes an ingress-protective housing 220 (hereinafter referred to interchangeably as "the housing 220"). The housing 220 is configured to enable removal of the impact-resistant energy core 300 and the first and second circuit boards 320, 330 during servicing. The housing 220 is configured to provide additional utility for withstanding daily activities encountered during a patient's continuous use of the wearable device 100. An ambulatory patient can, for example, wear the device 100 and the controller 200 for hours, days, and weeks continuously through activities such as walking, driving, sleeping, and bathing. By securely assembling the controller 200 around the impact-resistant, unitary mass that is the energy core 300, the high and low voltage components are securely affixed to withstand impact. By surrounding the controller with an ingress-protective housing 220, the energy core 300, first circuit board 320, second circuit board 330, and other components and circuitry, such as the therapy delivery circuit 202 and the user interface 208 (e.g. display and/or touch screen), are also protected from environmental impact, such as liquid and dust.

In implementations, the impact-resistant energy core 300 and the affixed first and second circuit boards 320, 330 occupy between about 25%-90% of a volume defined by the ingress-protective housing 220. This reduces the amount of volume in which dust or liquid could accumulate in addition to providing a compact controller 200 more comfortably worn and handled by a patient. As depicted in the exploded views of FIGS. 5 and 10, for example, the ingress-protective housing comprises a rear shell 220b configured to be disposed adjacent the second circuit board 330 and a front shell 220a configured to be disposed adjacent the first circuit board 320, the front shell 220a mating with the rear shell 220b in a sealed configuration. Although the front shell 220a and rear shell 220b are described herein as "front" and "rear," these terms are purely illustrative for describing implementations of characteristics and features associated with each of two shells. The terms "front" and "rear" could be applied in the alternative.

In some implementations, the ingress-protected housing on the controller 200 is water-resistant and has a predetermined ingress protection rating complying with one or more of the rating levels set forth in IEC standard 60529. The liquid Ingress Protection rating can be one or more of any level (e.g., levels 3 to 9) in which rating compliance tests are specified in the standard. For example, to have a liquid ingress protection rating level of 6, the ingress-protected housing 220 of the controller 200 shall protect against ingress of water provided by a powerful water jet. The powerful water jet test requires that the housing of the controller 200 is sprayed from all practicable directions with a stream of water from a test nozzle having a 12.5 mm diameter. Water sprays for 1 minute per square meter for a minimum of three minutes at a volume of 100 liters per minute (+/−5 percent) so that a core of the stream of water is a circle of approximately 120 mmm in diameter at a distance of 2.5 meters from the nozzle. For example, to have a rating level of 7, ingress of water shall not be possible when the housing of the controller 200 is completely immersed in water at a depth between 0.15 m and 1 m so that the lowest point of the housing of the controller 200 with a height less than 850 mm is located 1000 mm below the surface of the water and the highest point of a housing of the controller 200 with a height less than 850 mm is located 150 mm below the surface of the water. The controller 200 is immersed for a duration 30 minutes, and the water temperature does not differ from that of the housing of the controller 200 by more than 5K.

In implementations, the assembled ingress-protective housing 220 of the controller 200 can be constructed to be water-resistant and tested for such in accordance with the IEC 60529 standard for Ingress Protection. For instance, the controller 200 of the device 100 may be configured to have a rating of level 7, protecting against immersion in water, up to one meter for thirty minutes. This enables a patient to wear the device 100 in the bathtub or shower for uninterrupted, continuous use. In implementations, the controller 200 of the device 100 may be multiple coded, including two or more levels. For example, the controller 200 of the device 100 can maintain a liquid Ingress Protection level of 7, protecting against temporary immersion, and a liquid Ingress Protection level of 5, protecting against water jets. In implementations, the ingress-protective housing includes an IP67 rating as set forth in IEC 60529 Standard for Ingress Protection, and the controller 200 of the device 100 can maintain a liquid Ingress Protection level of 6, protecting against powerful water jets, and a liquid Ingress Protection level of 7, protecting against temporary immersion. In examples, the ingress-protective housing 220 of the controller 200 can comprise or consist of at least one of neoprene, thermoformed plastic, or injection molded rubber or plastic, such as silicone or other biocompatible synthetic rubber.

The ingress-protected housing 220 of the controller 200 therefore protects the components thereunder (e.g., the processor 218, the therapy delivery circuit 202 including a polarity switching component such as an H-bridge 228, a data storage 204, a network interface 206, a user interface 208, at least one battery 210, the sensor interface 211, an alarm manager 213, and the at least one capacitors 240) from external environmental impact, for example damage associated with solid particle ingress, dust ingress, and/or moisture, water vapor or liquid ingress. Preventing ingress protects the electronic components of the device 100 from short-circuiting or corrosion of moisture-sensitive electronics, for example, when a patient wears the device while showering.

Figure 10B:
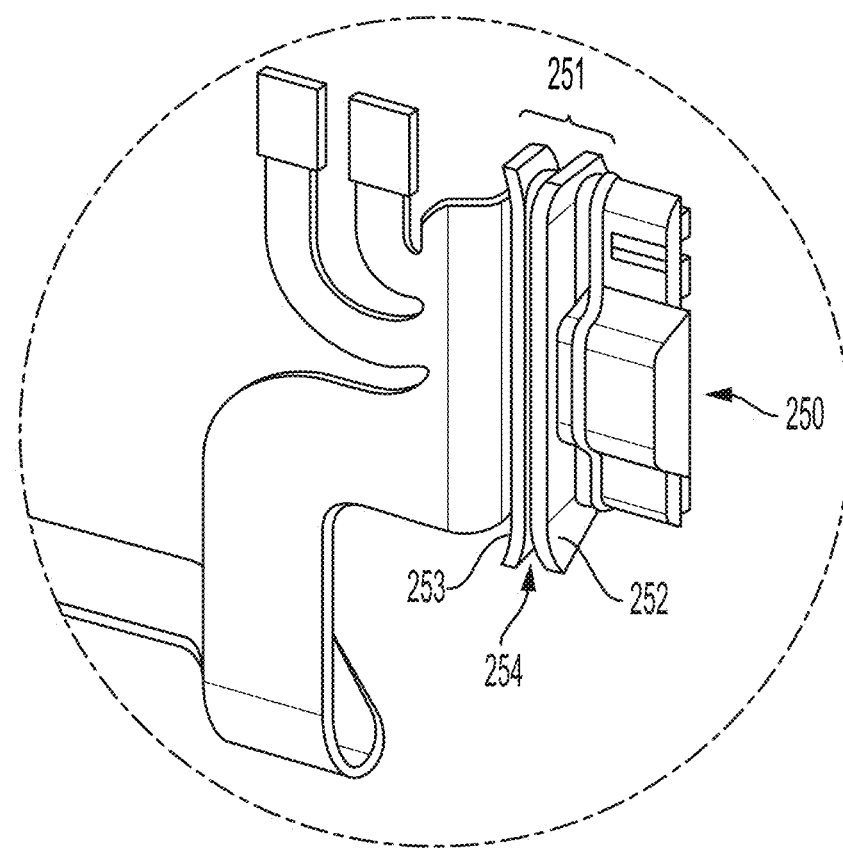
FIG. 10B depicts a magnified view of a gasket portion of the enclosure of FIG. 10A.
Figure 11A:
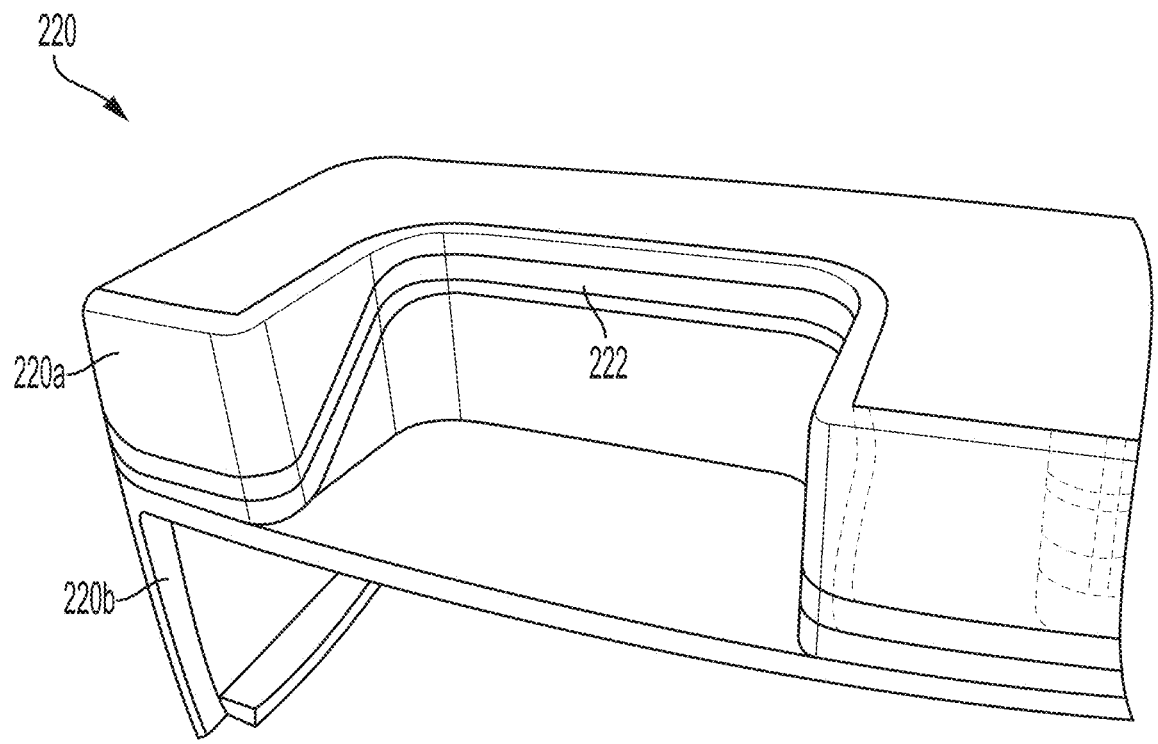
FIG. 11A depicts a perspective side view of an example assembled device controller for a wearable cardiac monitoring and treatment device.
Figure 11B:
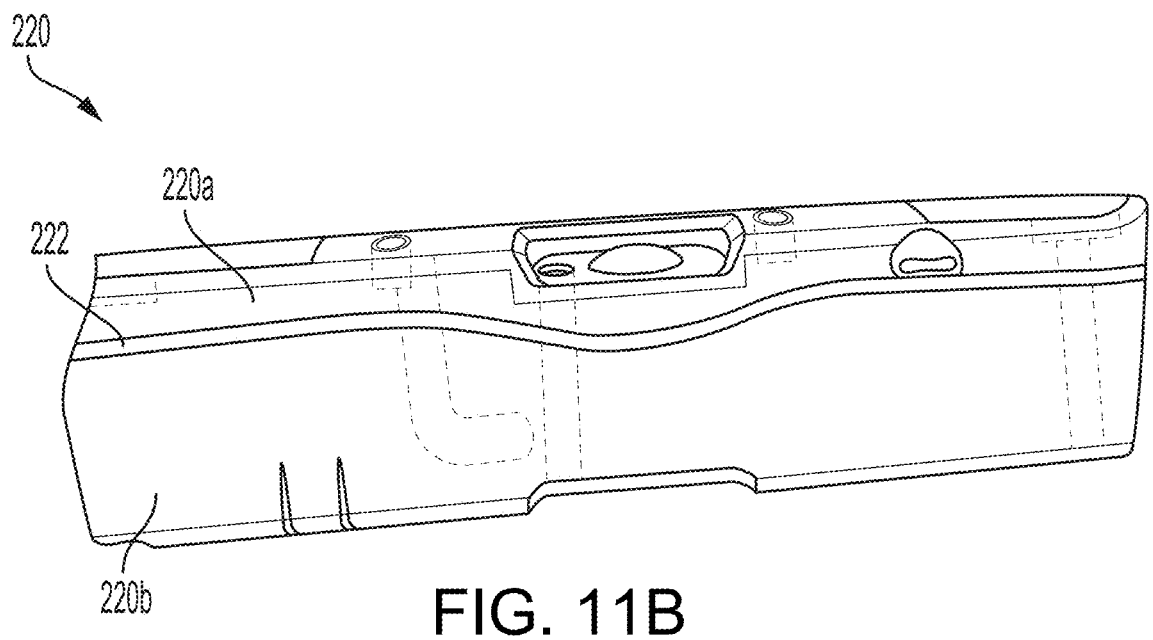
FIG. 11B depicts top view of an example assembled device controller for a wearable cardiac monitoring and treatment device.
Figure 12:
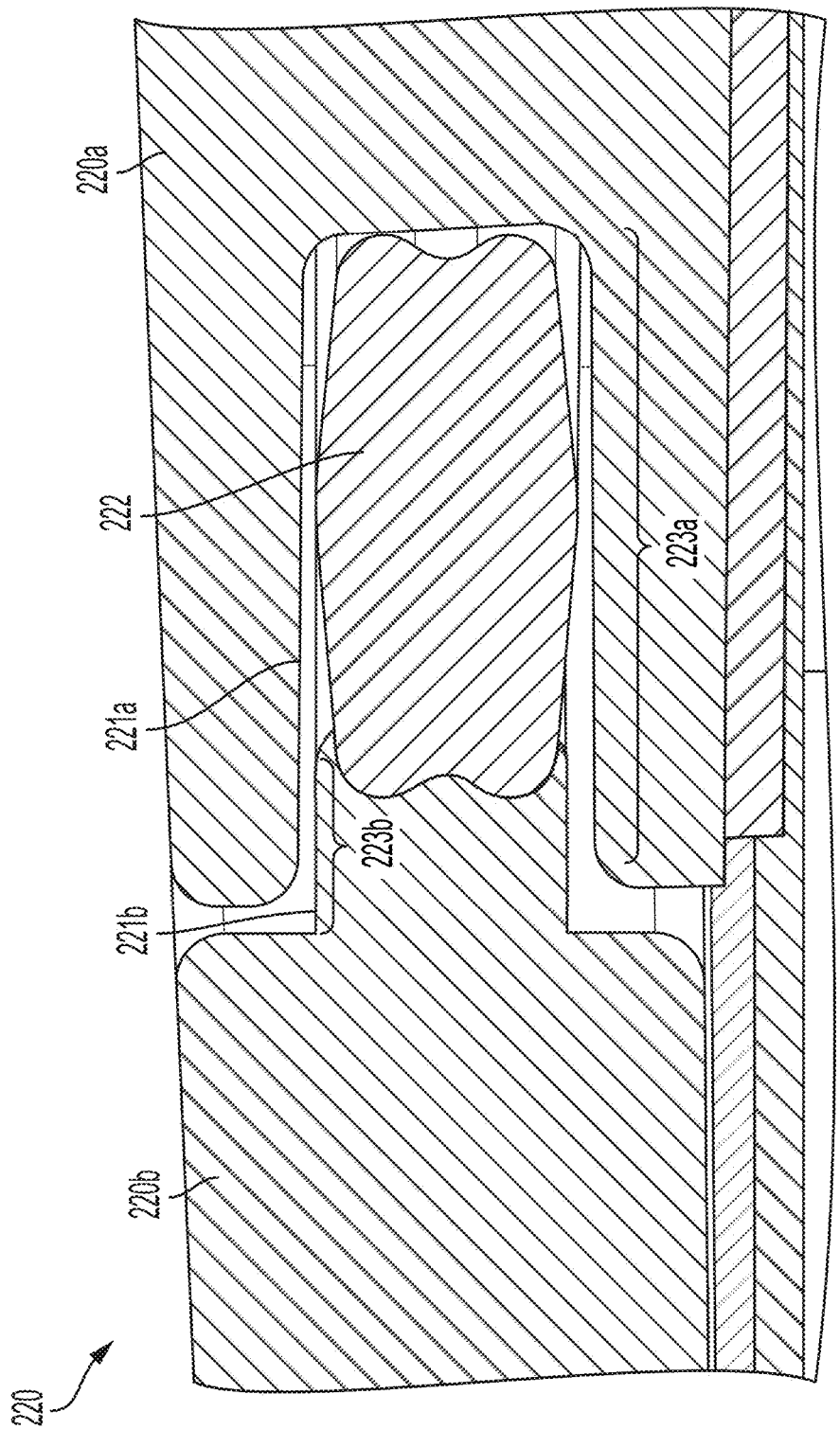
FIG. 12 depicts a schematic cross section of a mating portion of an example assembled device controller for a wearable cardiac monitoring and treatment device.

In implementations, for example, the two interlocking shell portions, e.g. the front shell 220a and rear shell 220b, are configured to be mated in a sealed press fit. For example, as shown in FIGS. 10-11B, a compressible grommet, O-ring, or silicone seal 222 can be inserted between and/or about the mating surfaces such that ingress into the interlocked shell portions is prevented. As shown in FIG. 12, for example, a mating edge 221a of the front shell 220a and a mating edge 221b of the rear shell 220b are configured to engage in a fitted interlock when the front and rear shells 220a, 220b are mated to form the ingress-protective housing 220. In implementations, at least one of the front and rear shells 220a, 220b includes a mortise in the mating edge and the other of the front and rear sells includes a projection configured to engage the mortise. In implementations, such as the embodiment depicted in FIG. 12, the front shell 220a includes a mortise 223a on its mating edge 221a and the rear shell 220b includes a projection 223b its mating edge 221b configured to engage the mortise of the mating edge 221a front shell 220a. The fitted interlock can include a compressible silicone seal 222 disposed in the mortise 223a. For example, in implementations such as that shown in FIG. 11, the compressible silicone seal 222 has a cross sectional "H" profile and provides resistance to taking a compression set such that the mated seal is tightly held and impervious to ingress of liquid and particulates. In implementations, the compressible silicone seal 222 has a durometer in a range of about 10 to 90 Shore A.

In implementations, the front and rear shells 220a, 220b can be held in a sealed configuration by a press fit. Additionally or alternatively, in implementations, the front and rear shells 220a, 220b can be held in a sealed configuration by one or more releasable fasteners. For example, as shown in the exploded assembly of FIGS. 5, the front and rear shells 220a, 220b can be held in a sealed configuration by plurality of screws 232. In implementations, each of the plurality of screws 232 is configured to be inserted through each of a corresponding one of a plurality of holes in 234 in the front shell 220a and engage each of a corresponding one of a plurality of screw bosses 236a-e disposed on an internal surface of the rear shell 220b. In implementations, the housing 220 can include one or more clips 238 disposed on one of the front and rear shells 220a, 220b for engaging the other of the front and rear shells. In implementations such as that of FIGS. 5 and 10, the rear shell 220b includes a clip 238 formed with the rear shell as a flexible tab configured for holding the front shell 220a in mated engagement. In implementations, a single flexible tab along one edge of the front shell 220a or rear shell 220b enables mating the two shell portions of the housing 220 and holding them together while the plurality of holes 234 and corresponding plurality of screw bosses 236 are aligned for receiving the plurality of screws therein. In implementations, the one or more clips 238 includes flexible tab about 0.5 to 1.0" long. As shown in FIG. 7, in implementations, the clip 238 can include a barbed free end configured to engage a retaining trough 235 on the opposing shell.

Returning to FIG. 5, the plurality of holes 234 in the front shell 220a can be sealed for maintaining an ingress protective rating of IP67 for the housing 220. In implementations, each of the plurality of holes can include disposed therein rubber O-rings or grommets for sealing the holes 234 against ingress of liquid and particulate matter. Additionally or alternatively, as shown in FIG. 5, the housing 220 can include one or more impervious plates configured to be secured over the one or more releasable fasteners to prevent ingress of liquid and particulate matter. For example, the two plates 239a, 239b are configured to be attached to the front shell 220a, thereby covering the holes 234a-e and screws 232a-e disposed therein. The one or more impervious plates, e.g. plates 239a, 239b, can be releasably attached to the exterior surface of the front shell 220a by at least one of a press fit engagement, adhesive tape, snaps, or clips.

The one or more plates are releasably attached so that the releasable fasteners, e.g. the plurality of screws 232a-e, are accessible for removal from the housing 220 during servicing of the controller 200. In implementations, the front shell 220a and the rear shell 220b are configured to be separated for removal and replacement of at least the impact-resistant energy core 300 and the affixed first and second circuit boards 320, 330. As shown in FIGS. 5 and 10, the front shell 220a can include a touch screen 225 for interacting with the display 329 and a speaker 227 for providing audible alarms, notifications, and instructions to a patient and/or bystander. The first and second plates 239a, 239b can be sized and shaped to follow the contours of the front shell 220a such that the touch screen 225 is accessible and uncovered with the first and second plates 239a, 239b affixed to the front shell 220a. Additionally, the at least one plate, e.g. plate 239a, can include a plurality of apertures 241 configured to be positioned adjacent a plurality of speaker openings 242 in the front shell 220a for unobstructed transmission of audible messages, alarms, and notifications.

In implementations, the touch screen 225 is disposed on an interior surface of the front shell 220a. The touch screen 225 can be affixed to the front shell with an ingress-protective sealant such that the assembled ingress-protective housing 220 maintains an IP67 rating. Similarly, in implementations, the speaker 227 is disposed on an interior surface of the front shell 220a. The speaker 227 can be sealed with an ingress-protective sealant such that the assembled ingress-protective housing 220 maintains an IP67 rating. Additionally or alternatively, in implementations, the front shell 220a can include a particulate catching screen disposed across the speaker opening for preventing ingress of particulate matter and liquid as prescribed by the IP67 rating. In implementations, the speaker 227 can be adhered to the front shell 220a by a curing adhesive, such as DP100 epoxy. Additionally or alternatively, the speaker can be adhered to the front shell 220a of the housing 220 by a double sided, pressure sensitive adhesive tape. During servicing, such as cleaning or refurbishing, the housing 220 can be disassembled and the front shell 220a, along with the used and potentially dusty and dirty touch screen 225 and speaker 227, can be removed and replaced by a new assembly of the same elements assembled and sealed similarly for maintaining an IP67 ingress protection rating.

Any additional openings in the housing 220 can be similarly sealed to prevent ingress, such as any openings comprising user input buttons 343a, 343b or electronics ports for mating with wired components. In some examples, ports for receiving connectors therein can be sealed to the housing 220 to prevent ingress. In implementations, the ingress-protected housing 220 of the controller 200 includes at least one ingress-protected receiving port 250 configured to receive at least one connector 256 configured to electrically couple a plurality of ECG sensing electrodes 212 and therapy electrodes 214 to the controller 200. As previously described, the plurality of ECG sensing electrodes 212 and therapy electrodes 214 can be in continuous extended contact with the torso 5 of the patient to monitor for and treat a cardiac arrhythmia in the patient. In implementations, the plurality of ECG sensing electrodes 212 are configured to sense an ECG signal of the patient for further analysis by at least one processor 218 disposed on the first circuit board 320.

The controller 200 can be in separable electrical communication with the plurality of ECG sensing electrodes 212 and therapy electrodes 214. The separable electrical communication includes the connector 256 in communication with the plurality of ECG sensing electrodes 212 and plurality of therapy electrodes 214. The connector 256 can be mated to the ingress-protective housing 220 via the receiving port 250 such that the connector 256 and the plurality of ECG sensing electrodes 212 and plurality of therapy electrodes 214 are in electrical communication with one or both of the first and second circuit boards 320, 330. The receiving port 250 can be in electrical communication with one or both of the first and second circuit boards 320, 330 via, for example, one or more flexible cable connectors 255 as shown in FIG. 10.

In implementations, the at least one ingress-protected receiving port 250 can have an IP67 rating such that the device 100 can be connected to the controller 200 and operable when a patient is showering or bathing, for example. As shown in FIGS. 10A-B, the ingress-protected receiving port 250 can include a grommet 251 configured to receive mating edges of the front and rear shells 220a, 220b in the assembled configuration of the ingress-protective housing 220. As shown in FIG. 10B, the grommet 251 includes an upper flange 252 and a lower flange 253 and a well 254 therebetween to receive the mating edges of the front and rear shells therein. Additionally or alternatively, the grommet 251 can be sealed to the assembled housing 220 with an ingress-protective sealant. The grommet 251 can be made of at least one of compressible rubber, polyurethane, silicone, and any thermoplastic elastomer, such that the intersection of the front and rear shells 220a, 220b with the grommet 251 maintains an ingress-protection rating of IP67.

Figure 15:
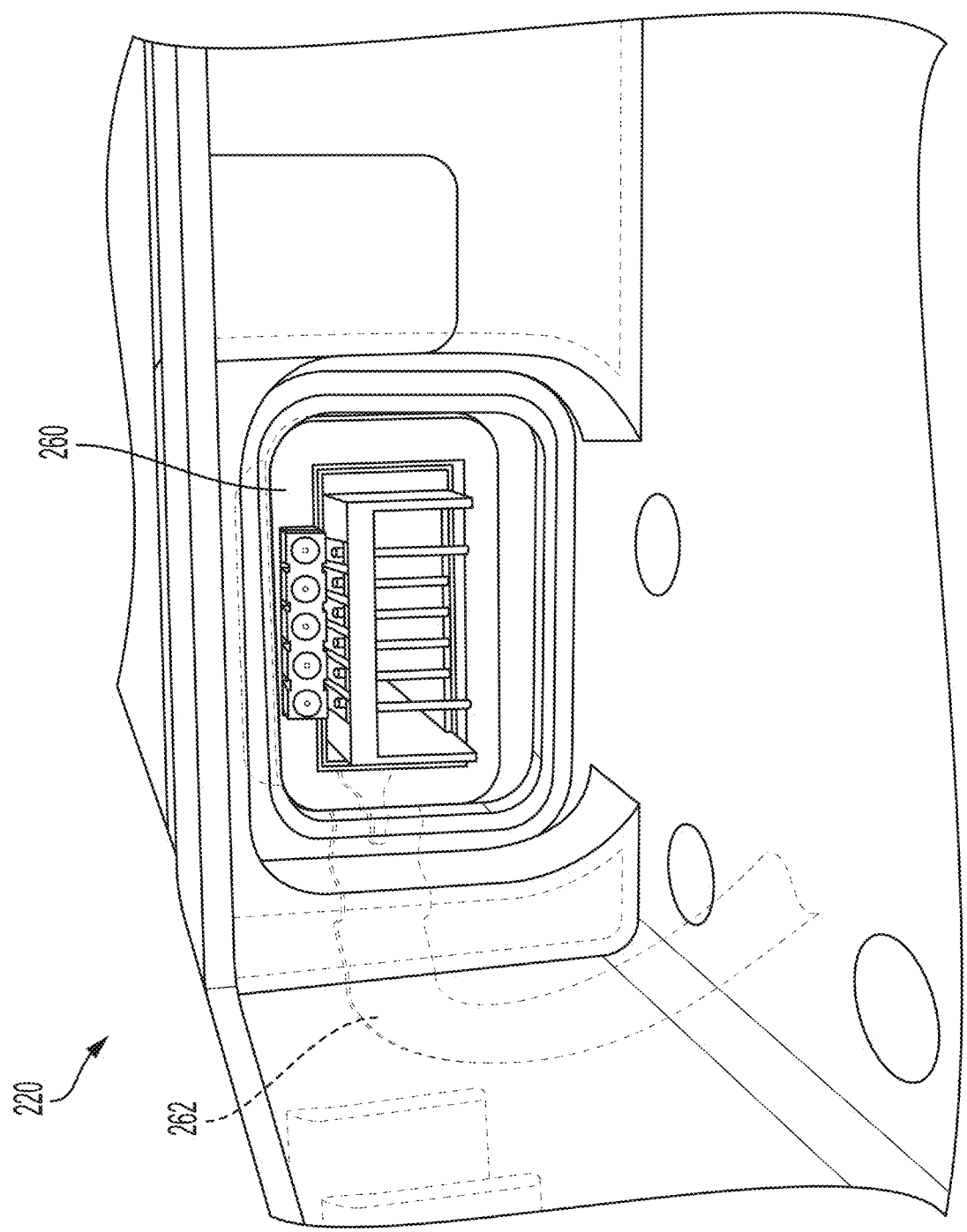
FIG. 15 depicts an example battery connector for a device controller for a wearable cardiac monitoring and treatment device.

Turning now to FIGS. 14A-15, additional openings in the housing 220 can include an opening for a battery connector 260. In implementations, the rear shell 220b further comprises a battery connector 260 extending therethrough for receiving a complimentary connector of a removable battery 210. As depicted in FIG. 15, the battery connector 260 can be sealed to the housing 220 with an ingress-protective sealant and can be in wired communication with at least one processor 218 disposed on the first circuit board 320. The wired communication can include, for example, a flexible cable connector 262 disposed between the energy core 300 and an interior surface of the rear shell 220b. The flexible cable connector 262 therefore extends between the battery connector 260 and the first circuit board 320 within the ingress protective housing 220 thereby electrically connecting the battery connector 262 to the first circuit board 320. In implementations, the ingress-protective sealant is at least one of epoxy and pressure sensitive adhesive. For example, the battery connector 260 can be affixed and sealed to the housing 220 by a compound such as an epoxy, e.g. DP100 epoxy. Additionally, or alternatively, the battery connector 260 can be affixed to the housing by pressure sensitive adhesive.

Returning to FIGS. 14A-B, in implementations, the rear shell 220b defines a compartment 270 configured to receive therein a removable battery module 215 containing the battery 210. Outer surfaces of the removable battery module 215 are flush with outer surfaces of the ingress-protective housing 220 in a mated configuration. As previously described with regard to FIGS. 8 and 9 the frame 310 can include an overhang portion 327 extending beyond the mouth 313 of the pocket 312 such that the entire length of the first circuit board 320 is disposed on the entire length of the frame 310 while the relatively shorter second circuit board 330 does not extend over the overhang portion 327. The overhang portion 327 therefore is configured to receive therein the compartment 270 formed in the rear shell 220b of the ingress-protective housing 220 for receiving the battery module 215. In implementations, a largest wall of the compartment nests within the overhang portion 327 of the frame 310 such that the wall of the compartment is substantially parallel to and adjacent to the portion of the first circuit board 320 disposed on the overhang portion 327 of the frame 310.

Figure 16:
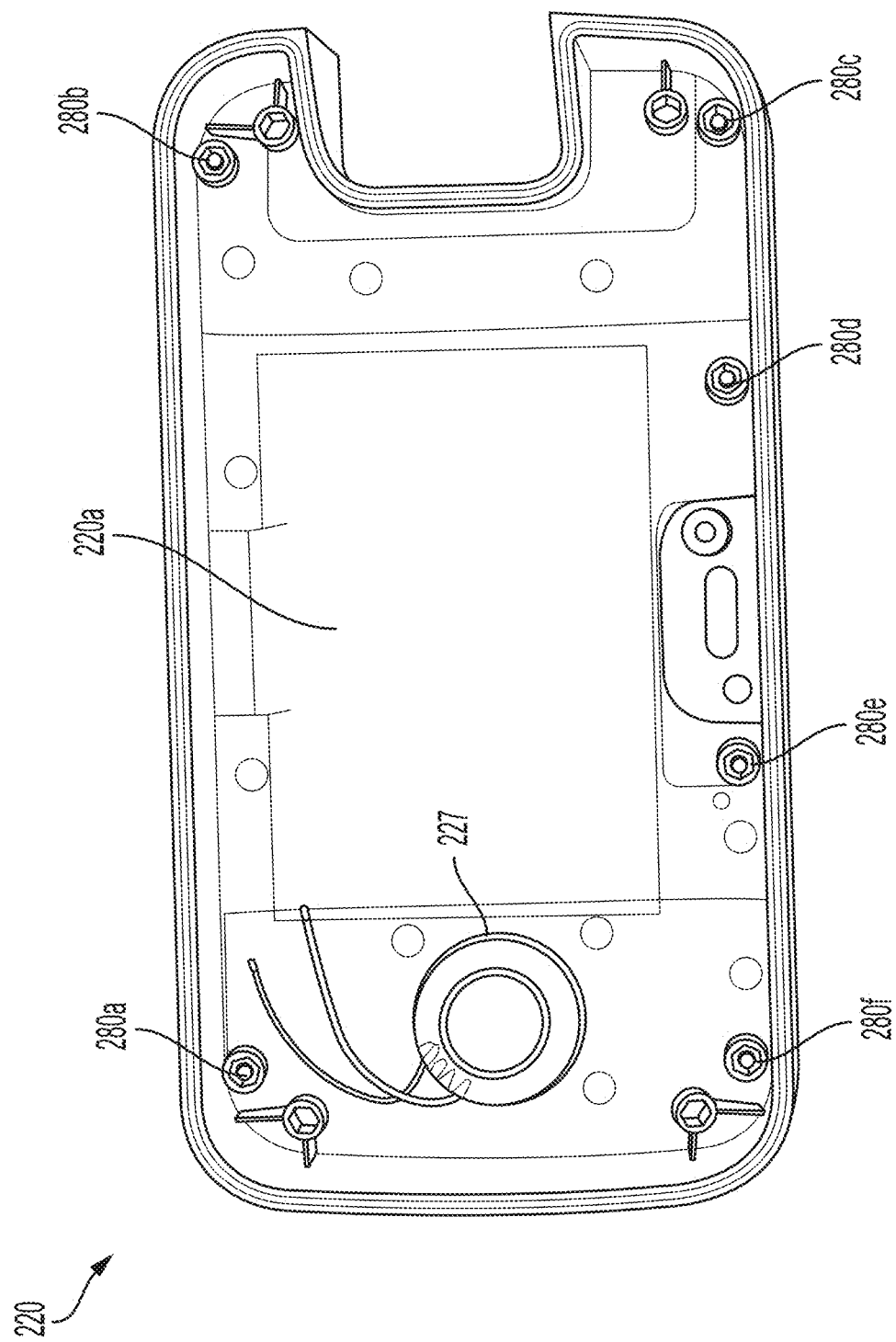
FIG. 16 depicts a plan view of an internal surface of an example housing for a device controller for a wearable cardiac monitoring and treatment device.

While the overhang portion 327 provides support for and prevents flexure of the first circuit board 320, the device 100 also can include additional impact-resistant features for further ruggedizing the controller 200 to withstand wear, stress, and impact associated with daily use. For example, as shown in FIG. 16, an interior surface of the front shell 220a includes one or more impact-resistant features for protecting the energy core 300 and the first and second circuit boards 320, 330. In implementations, the front shell 220a includes at least at least one shock absorbing spacer 280a-f configured to protect the impact-resistant energy core 300 and the affixed first and second circuit boards 320, 330 from mechanical impact. Additionally or alternatively, the rear shell 220b includes at least at least one shock absorbing spacer configured to protect the impact-resistant energy core 300 and the affixed first and second circuit boards 320, 330 from mechanical impact. If the controller 200 receives an impact, the energy core 300 and the first and second circuit boards 320, 330 deform into the at least one shock absorbing spacer and the first and second circuit boards 320, 330 do not flex. This protects the high voltage and low voltage circuitry the components mounted to the first and second circuit boards 320, 330 against damage from forces or torque associated with board flexure. The ingress-protective housing 220, therefore, is designed for rugged use and protects the components therein from damage. Simultaneously, the ingress-protective housing 220 enables servicing for maintenance and refurbishing of the controller 200 for use by another patient.

Figure 20:
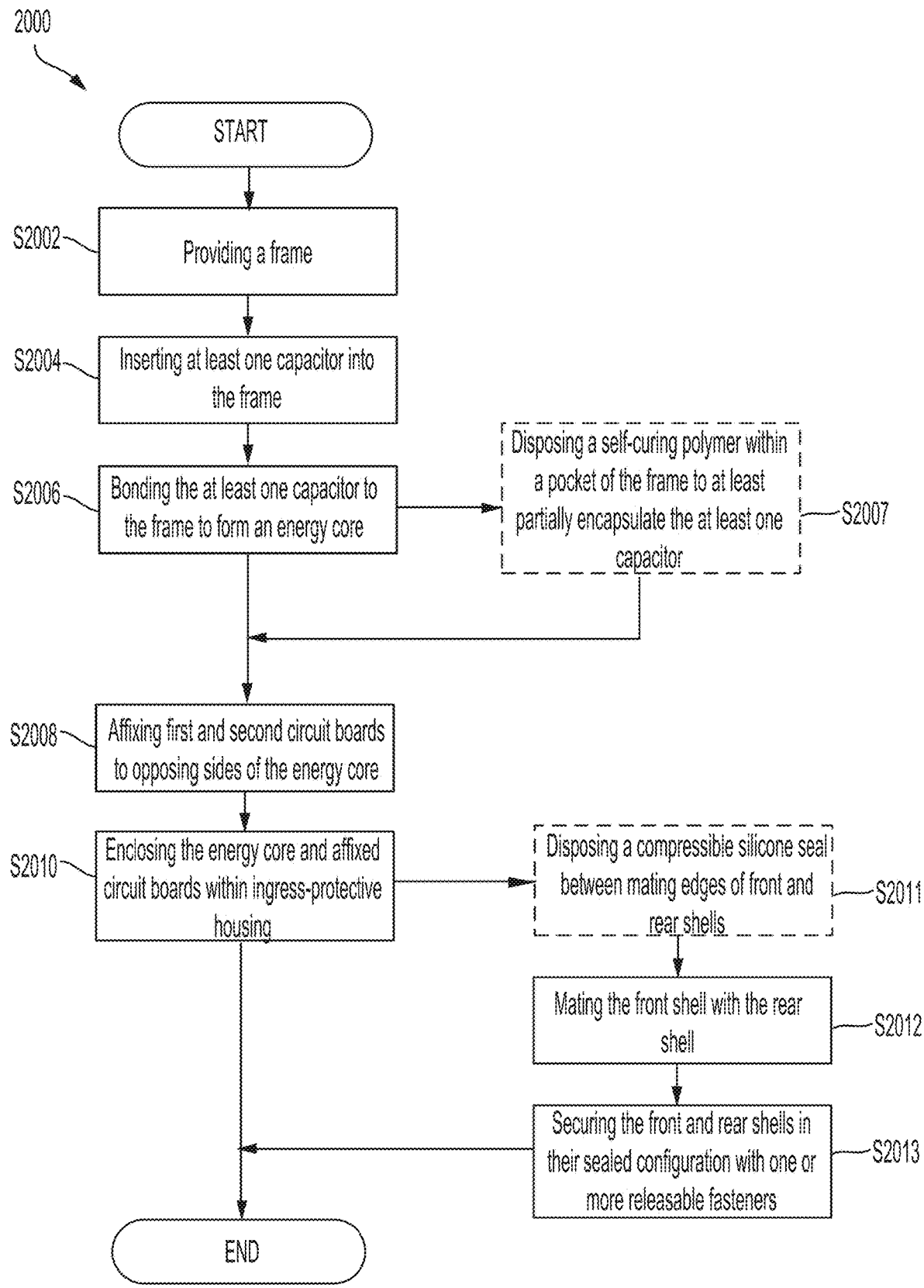
FIG. 20 depicts an example method of constructing a serviceable wearable cardiac treatment device controller for continuous extended use by an ambulatory patient.

In implementations, such as that of FIG. 20, a method of constructing 2000 a serviceable wearable cardiac treatment device controller 200 for continuous extended use by an ambulatory patient includes providing S2002 a frame 310 and inserting S2004 at least one capacitor 240 into the frame. The at least one capacitor can be configured to hold electrical charge sufficient to treat a cardiac arrhythmia of a patient. The method includes bonding S2006 the at least one capacitor to the frame such that the frame along with the bonded at least one capacitor comprises an impact-resistant energy core 300. The method includes affixing S2008 first and second circuit boards 320, 330 to opposing sides of the impact-resistant energy core in a manner to allow for separation from the impact-resistant energy core during service. The first and second circuit boards include cardiac arrhythmia monitoring and therapy circuitry in electrical communication with the at least one capacitor. The method includes enclosing S2010 the energy core and the affixed first and second circuit boards within an ingress-protective housing 220 configured to enable removal of the impact-resistant energy core and the first and second circuit boards during service.

In implementations, the frame 310 includes a pocket 312 for receiving therein the at least one capacitor therein. Bonding the at least one capacitor to the frame includes disposing S2007 a self-curing polymer within the pocket to at least partially encapsulate the at least one capacitor and thereby immovably bind the at least one capacitor to the frame to form a unitary mass.

As described previously with regard to embodiments of the device controller 200, the ingress-protective housing can include a rear shell 220b configured to be disposed adjacent the second circuit board and a front shell 220a configured to be disposed adjacent the first circuit board. In implementations of the method of constructing the serviceable wearable cardiac treatment device controller includes enclosing the energy core and the affixed first and second circuit boards within an ingress-protective housing by mating S2012 a front shell with the rear shell in a sealed configuration. The method can include securing S2013 the front and rear shells in their sealed configuration with one or more releasable fasteners 232a-e.

Mating the front and rear shell can include engaging a mating edge of the front shell and a mating edge of the rear shell in a fitted interlock to form the ingress-protective housing. In implementations, mating the front and rear shells comprises engaging a mortise 223a disposed on a mating edge of one of the front and rear shells with a projection 223b disposed on a mating edge of the other of the one of the front and rear shells. The method can further include disposing S2011 a compressible silicone seal 222 in the mortise to achieve an ingress-protective rating of at least one of IP6X, IPX6, and IPX7, where "X" is a variable representing a rating on a scale of 1 through 9 as set forth in the IEC 60529 Standard for Ingress Protection.

As described above, the teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, and other similar wearable medical devices.

A wearable medical cardiac monitoring device is capable of continuous use by the patient. Further, the wearable medical device can be configured as a long-term or extended use medical device. Such devices can be designed to be used by the patient for a long period of time, for example, a period of 24 hours or more, several days, weeks, months, or even years. Accordingly, the long period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for a long period of at least one year. In some implementations, the extended use can be uninterrupted until a physician or other caregiver provides specific instruction to the patient to stop use of the wearable medical device.

Regardless of the period of wear, the use of the wearable medical device can include continuous or nearly continuous wear by the patient as previously described. For example, the continuous use can include continuous wear of the wearable medical device by the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

In implementations, the patient-worn arrhythmia monitoring and treatment device 100 further includes a patient notification output via an output device such as the display 329. In response to detecting one or more treatable arrhythmia conditions, the processor 218 is configured to prompt the patient for a response by issuing the patient notification output, which may be an audible output, tactile output, visual output, or some combination of any and all of these types of notification outputs. In the absence of a response to the notification output from the patient, the processor is configured to cause the therapy delivery circuit 202 to deliver the one or more therapeutic pulses to the patient.

Figure 8:
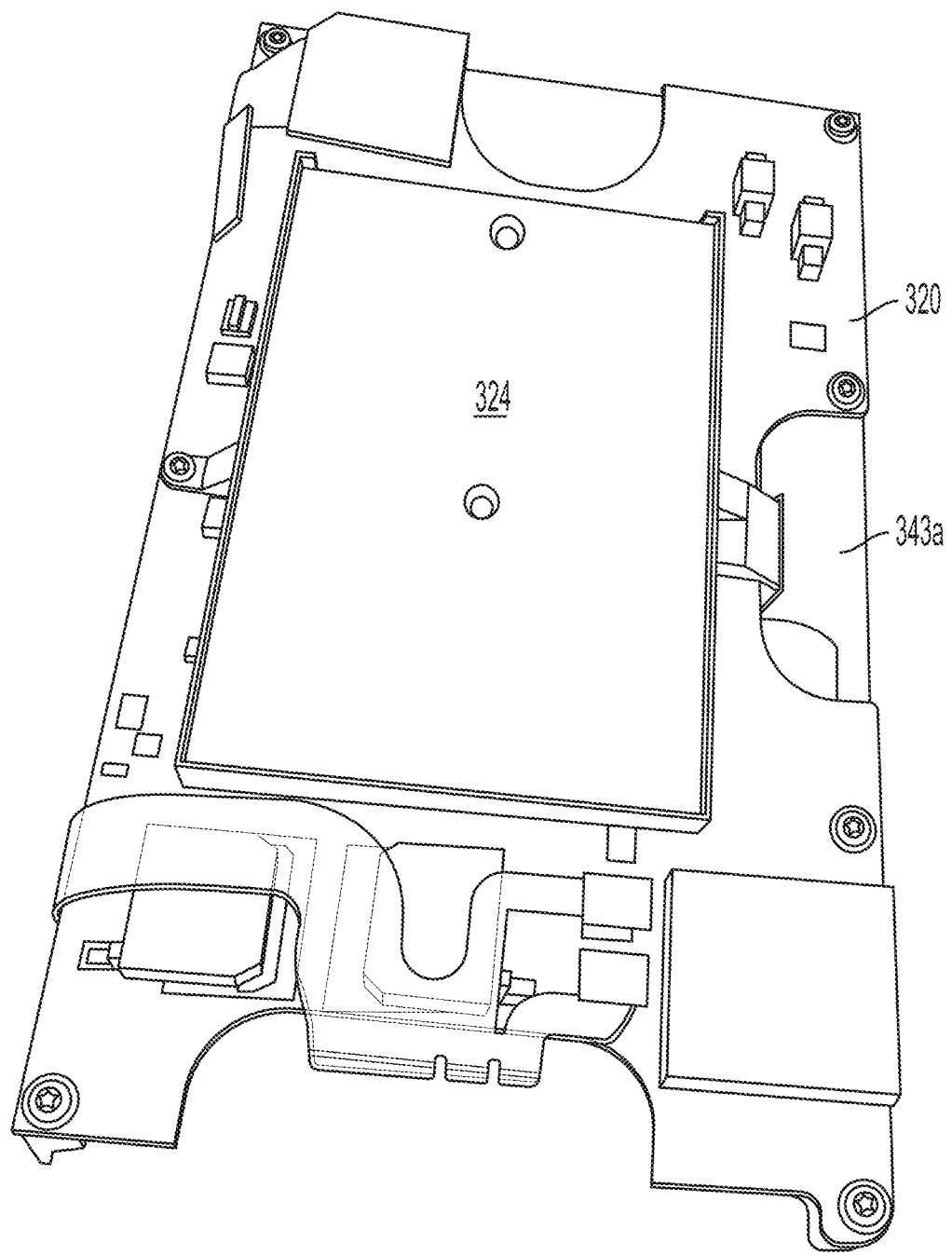
FIG. 8 depicts a front perspective view of an internal assembly of an example device controller for a wearable cardiac monitoring and treatment device.
Figure 17:
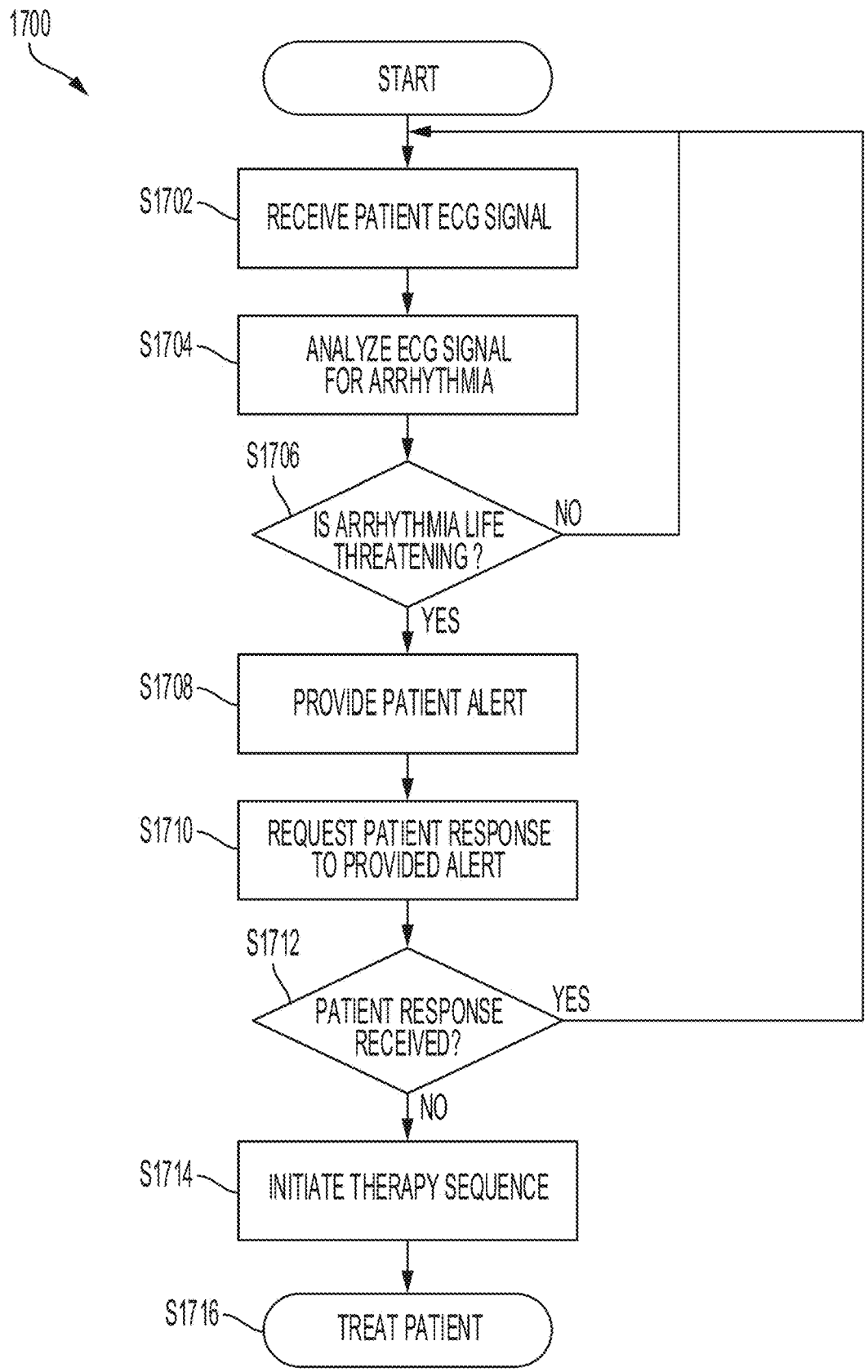
FIG. 17 is a schematic of an example method of using a wearable cardiac monitoring and treatment device.

FIG. 17 depicts an example of a process 1700 for determining whether to initiate a therapy sequence and apply a therapeutic pulse to the thoracic region of a patient. In implementations, the processor 218, receives S1702 a patient ECG signal from the ECG sensing electrodes 212 and analyzes S1704 the ECG signal for an arrhythmia condition. The processor 218 determines S1706 whether the arrhythmia is life threatening condition and requires treatment. If the arrhythmia is not life threatening, the processor 218 can cause a portion of the ECG signal to be stored in memory for later analysis and continue to monitor the patient ECG signal. If the arrhythmia is life threatening, the processor 218 provides S1708 a patient notification output and requests S1710 a patient response to the provided notification output. In implementations, the patient responds to an alert by interacting with a user interface (e.g., the user interface 208 of FIG. 2), which includes, for example, one or more buttons (e.g. the at least one button 343a, 343b of the device 100 as shown in FIGS. 8-10) or touch screen interface buttons with haptic feedback (e.g., touch screen buttons on the touch screen 225 of the controller 200 and/or a second at least one response button of a wearable article (e.g. an arm band or wrist worn article comprising at least one of a mechanically-actuatable button, a touch screen interface, and at least one touch screen button on a user interface of the wearable article) or like devices, such as smartphones running user-facing interactive applications). The response may be, for example, pressing one or more buttons in a particular sequence or for a particular duration. The processor 218 determines S1712 whether the patient response was received. If the patient responds to the notification output, the processor 218 is notified that the patient is conscious and returns to a monitoring mode, thereby delaying delivery of a therapeutic defibrillation or pacing shock. If the patient is unconscious and unable to respond to the provided alert, the processor 218 initiates S1714 the therapy sequence and treats S1716 the patient with the delivery of energy to the thoracic region of the patient. In implementations, if a user response button is pressed for longer than a threshold duration (e.g. longer than 5 seconds), the processor 218 instructs the device to prompt the patient to release the button. If the user response button is not released the device will return to a state of imminent therapy delivery and will alert the patient to the imminent shock.

In examples, the medical device can include physiological sensors configured to detect one or more cardiac signals. Examples of such signals include ECG signals and/or other sensed cardiac physiological signals from the patient. In certain implementations, the physiological sensors can include additional components such as accelerometers, vibrational sensors, and other measuring devices for recording additional parameters. For example, the physiological sensors can also be configured to detect other types of patient physiological parameters and vibrational signals, such as tissue fluid levels, cardio-vibrations, pulmonary-vibrations, respiration-related vibrations of anatomical features in the airway path, patient movement, etc. Example physiological sensors can include ECG sensors including a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

In examples, the physiological sensors can include a heart rate sensor for detecting heart beats and monitoring the heart rate of the patient. For instance, such heart rate sensors can include the ECG sensors and associated circuitry described above. In some examples, the heart rate sensors can include a radio frequency based pulse detection sensor or a pulse oximetry sensor worn adjacent an artery of the patient. In implementations, the heart rate sensor can be worn about the wrist of a patient, for example, incorporated on and/or within a watch or a bracelet. In some examples, the heart rate sensor can be integrated within a patch adhesively coupled to the skin of the patient over an artery.

In some examples, the treatment electrodes 114, 214 can also be configured to include sensors configured to detect ECG signals as well as other physiological signals of the patient. The ECG data acquisition and conditioning circuitry is configured to amplify, filter, and digitize these cardiac signals. One or more of the treatment electrodes 114, 214 can be configured to deliver one or more therapeutic defibrillating shocks to the body of the patient when the medical device determines that such treatment is warranted based on the signals detected by the ECG sensing electrodes 112, 212 and processed by the processor 218. Example treatment electrodes 114, 214 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). The therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

FIG. 2 illustrates an example component-level view of the controller 200. As shown in FIG. 7, the controller 200 can include a therapy delivery circuit 202 including a polarity switching component such as an H-bridge 228, a data storage 204, a network interface 206, a user interface 208 at least one battery 210, a sensor interface 211 that includes, for example, an ECG data acquisition and conditioning circuit, an alarm manager 213, least one processor 218, and one or more capacitors 240. A patient monitoring medical device can include components like those described with regard to FIG. 7, but does not include the therapy delivery circuit 202.

The therapy delivery circuit 202 is coupled to two or more treatment electrodes configured to provide therapy to the patient. For example, the therapy delivery circuit 202 includes, or is operably connected to, circuitry components that are configured to generate and provide the therapeutic shock. The circuitry components include, for example, resistors, one or more capacitors, relays and/or switches, an electrical bridge such as an H-bridge 228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the treatment electrodes 114, 214 has a conductive surface adapted for placement adjacent the patient's skin and has an impedance reducing means contained therein or thereon for reducing the impedance between a treatment electrode and the patient's skin. In implementations, each of the treatment electrodes can include a conductive impedance reducing adhesive layer, such as a breathable anisotropic conductive hydrogel disposed between the treatment electrodes and the torso of the patient. In implementations, a patient-worn cardiac monitoring and treatment device may include gel deployment circuitry configured to cause the delivery of conductive gel substantially proximate to a treatment site (e.g., a surface of the patient's skin in contact with the treatment electrode 114) prior to delivering therapeutic shocks to the treatment site. As described in U.S. Pat. No. 9,008,801, titled "WEARABLE THERAPUETIC DEVICE," issued on Apr. 14, 2015 (hereinafter the "'801 patent"), which is incorporated herein by reference in its entirety, the gel deployment circuitry can be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry can be coupled to or integrated with each of the treatment electrodes 114, 214.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the treatment electrode can be integrated into a treatment electrode assembly that can be removed and replaced as a single unit either after use, or if damaged or broken.

Continuing with the description of the example medical device of FIG. 2, in implementations, the at least one capacitors 240 is a plurality of capacitors (e.g., two, three, four or more capacitors) comprising a capacitor bank. The plurality of capacitors can be switched into a series connection during discharge for a defibrillation pulse. For example, four capacitors of approximately 650 g can be used. In one implementation, the capacitors can have between 200 to 2500 volt surge rating and can be charged in approximately 5 to 30 seconds from a battery 210 depending on the amount of energy to be delivered to the patient. In another example, the at least one capacitor is two capacitors shorted together in parallel electrical communication. The two capacitors can have combined capacitance of 162.5 g and a volt surge rating of between 1000 and 2000 V.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device. In certain implementations, the data storage 204 can include executable instructions that, when executed, are configured to cause the processor 218 to perform one or more functions.

In some examples, the network interface 206 can facilitate the communication of information between the medical device and one or more other devices or entities over a communications network. For example, the network interface 206 can be configured to communicate with a remote computing device such as a remote server or other similar computing device. The network interface 206 can include communications circuitry for transmitting data in accordance with a BLUETOOTH wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a WI-FI communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device. In some implementations, the user interface 208 can be implemented as a wearable article or as a hand-held user interface device (for example, wearable articles including the patient interface pod 140 of FIG. 1 and the wrist and arm worn remote devices.) For instance, a hand-held user interface device can be a smartphone or other portable device configured to communicate with the processor 218 via the network interface 206. In an implementation, the hand-held user interface device may also be the intermediary device for facilitating the transfer of information from the device to a remote server.

As described, the medical device can also include at least one battery 210 configured to provide power to one or more components, such as the at least one capacitor 240. The battery 210 can include a rechargeable multi-cell battery pack. In one example implementation, the battery 210 can include three or more 2200 mAh lithium ion cells that provide electrical power to the other device components. For example, the battery 210 can provide its power output in a range of between 20 mA to 1000 mA (e.g., 40 mA) output and can support 24 hours, 48 hours, 72 hours, or more, of runtime between charges. As previously described in detail, in certain implementations, the battery capacity, runtime, and type (e.g., lithium ion, nickel-cadmium, or nickel-metal hydride) can be changed to best fit the specific application of the medical device.

The sensor interface 211 can be coupled to one or more sensors configured to monitor one or more physiological parameters of the patient. As shown in FIG. 2 the sensors can be coupled to the medical device controller (e.g., processor 218) via a wired or wireless connection. The sensors can include one or more sensing electrodes (e.g., ECG sensing electrode 212), vibrations sensors 224, and tissue fluid monitors 226 (e.g., based on ultra-wide band radiofrequency devices). For example, the sensor interface 211 can include ECG circuitry (such as ECG acquisition and conditioning circuitry) and/or accelerometer circuitry, which are each configured to receive and condition the respective sensor signals.

The sensing electrodes can monitor, for example, a patient's ECG information. For example, the sensing electrodes of FIG. 2 can be ECG sensing electrodes 212 and can include conductive electrodes with stored gel deployment (e.g., metallic electrodes with stored conductive gel configured to be dispersed in the electrode-skin interface when needed), conductive electrodes with a conductive adhesive layer, or dry electrodes (e.g., a metallic substrate with an oxide layer in direct contact with the patient's skin). The sensing electrodes can be configured to measure the patient's ECG signals. The sensing electrodes can transmit information descriptive of the ECG signals to the sensor interface 211 for subsequent analysis.

The vibrations sensors 224 can detect a patient's cardiac or pulmonary (cardiopulmonary) vibration information. For example, the cardiopulmonary vibrations sensors 224 can be configured to detect cardio-vibrational biomarkers in a cardio-vibrational signal, including any one or all of S1, S2, S3, and S4 cardio-vibrational biomarkers. From these cardio-vibrational biomarkers, certain electromechanical metrics can be calculated, including any one or more of electromechanical activation time (EMAT), percentage of EMAT (% EMAT), systolic dysfunction index (SDI), left ventricular diastolic perfusion time (LDPT), and left ventricular systolic time (LVST). The cardiopulmonary vibrations sensors 224 may also be configured to detect heart wall motion, for example, by placement of the cardiopulmonary vibrations sensor 224 in the region of the apical beat.

The vibrations sensors 224 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 224 are able to detect vibrations generated in the trachea or lungs due to the flow of air during breathing. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the cardiopulmonary vibrations information or patient position/movement to the sensor interface 211 for subsequent analysis.

The tissue fluid monitors 226 can use radio frequency (RF) based techniques to assess changes of accumulated fluid levels over time. For example, the tissue fluid monitors 226 can be configured to measure fluid content in the lungs (e.g., time-varying changes and absolute levels), for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 211 for subsequent analysis.

The sensor interface 211 can be coupled to any one or combination of sensing electrodes/other sensors to receive other patient data indicative of patient parameters. Once data from the sensors has been received by the sensor interface 211, the data can be directed by the processor 218 to an appropriate component within the medical device. For example, if cardiac data is collected by the cardiopulmonary vibrations sensor 224 and transmitted to the sensor interface 211, the sensor interface 211 can transmit the data to the processor 218 which, in turn, relays the data to a cardiac event detector. The cardiac event data can also be stored on the data storage 204.

An alarm manager 213 can be configured to manage alarm profiles and notify one or more intended recipients of events specified within the alarm profiles as being of interest to the intended recipients. These intended recipients can include external entities such as users (e.g., patients, physicians, other caregivers, patient care representatives, and other authorized monitoring personnel) as well as computer systems (e.g., monitoring systems or emergency response systems). The alarm manager 213 can be implemented using hardware or a combination of hardware and software. For instance, in some examples, the alarm manager 213 can be implemented as a software component that is stored within the data storage 204 and executed by the processor 218. In this example, the instructions included in the alarm manager 213 can cause the processor 218 to configure alarm profiles and notify intended recipients according to the configured alarm profiles. In some examples, alarm manager 213 can be an application-specific integrated circuit (ASIC) that is coupled to the processor 218 and configured to manage alarm profiles and notify intended recipients using alarms specified within the alarm profiles. Thus, examples of alarm manager 213 are not limited to a particular hardware or software implementation.

In some implementations, the processor 218 includes one or more processors (or one or more processor cores) that each are configured to perform a series of instructions that result in manipulated data and/or control the operation of the other components of the medical device. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to a specific input stimulus in a specific way and generates a corresponding output based on that input stimulus. In some example cases, the processor 218 can proceed through a sequence of logical transitions in which various internal register states and/or other bit cell states internal or external to the processor 218 can be set to logic high or logic low. The processor 218 can be configured to execute a function stored in software. For example, such software can be stored in a data store coupled to the processor 218 and configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor 218 can be a multi-core processor, e.g., a processor having two or more processing cores. The processor can be an Advanced RISC Machine (ARM) processor such as a 32-bit ARM processor or a 64-bit ARM processor. The processor can execute an embedded operating system and include services provided by the operating system that can be used for file system manipulation, display & audio generation, basic networking, firewalling, data encryption and communications.

In implementations, the therapy delivery circuit 202 includes, or is operably connected to, circuitry components that are configured to generate and provide the therapeutic shock. As described previously, the circuitry components include, for example, resistors, one or more capacitors 240, relays and/or switches, an electrical bridge such as an H-bridge 228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 202 and under control of one or more processors (e.g., processor 218) to provide, for example, one or more pacing or defibrillation therapeutic pulses.

In implementations, the device further includes a source of electrical energy, for example, the one or more capacitors 240, that stores and provides energy to the therapy delivery circuit 202. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses can be generated by charging the one or more capacitors 240 and discharging the energy stored in the one or more capacitors 240 into the patient. For example, the therapy delivery circuit 202 can include one or more power converters for controlling the charging and discharging of the one or more capacitors 240. In some implementations, the discharge of energy from the one or more capacitors 240 can be controlled by, for example, an H-bridge that controls the discharge of energy into the body of the patient, like the H-bridge circuit described in U.S. Pat. No. 6,280,461, titled "PATIENT-WORN ENERGY DELIVERY APPARATUS," issued on Aug. 28, 2001, and U.S. Pat. No. 8,909,335, titled "METHOD AND APPARATUS FOR APPLYING A RECTILINEAR BIPHASIC POWER WAVEFORM TO A LOAD," issued on Dec. 9, 2014, each of which is hereby incorporated herein by reference in its entirety.

Figure 18:
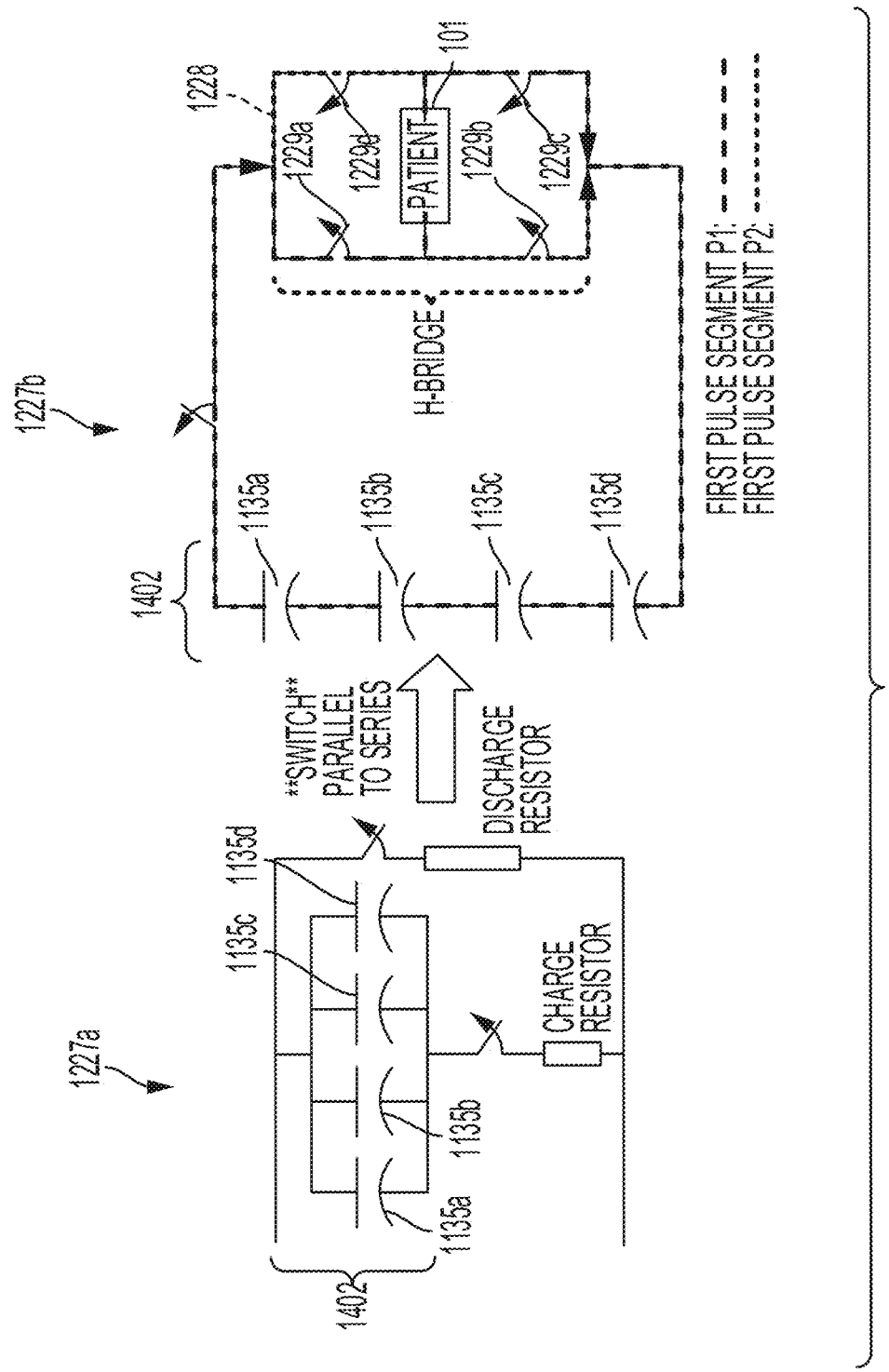
FIG. 18 depicts a schematic diagram of an embodiment of electrical components of a controller for a cardiac monitoring and treatment device.

As shown in the embodiment to FIG. 18, an H-bridge 1228 is electrically coupled to a capacitor bank 1402 including four capacitors 1135a-d that are charged in parallel at a preparation phase 1227a and discharged in series at a treatment phase 1227b. In some implementations, the capacitor bank 1402 can include more or fewer than four capacitors 1135. During the treatment phase 1227b, the H-bridge 1228 applies a therapeutic pulse that causes current to flow through the torso 5 of the patient 101 in desired directions for desired durations. The H-bridge 1228 includes H-bridge switches 1229a-d that are opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 1229a and 1229c, enables current to flow in a first direction for first pulse segment P1. Opening switches 1229a and 1229c and closing switches 1229b and 1229d enables current to flow through the torso 5 of the patient 101 in a second pulse segment P2 directionally opposite the flow of the first pulse segment P1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A serviceable wearable cardiac treatment device for continuous extended use by an ambulatory patient, comprising:
    a garment configured to dispose therein a plurality of ECG sensing and therapy electrodes configured to be in continuous extended contact with the patient to monitor for and treat a cardiac arrhythmia in the patient; and
    a device controller configured to be in separable electrical communication with the plurality of ECG sensing and therapy electrodes in the garment, the device controller comprising
        an impact-resistant energy core, comprising
            a frame, and
            at least one capacitor permanently bonded to the frame such that the frame along with the bonded at least one capacitor comprise a unitary mass, the at least one capacitor configured to hold electrical charge sufficient to treat the cardiac arrhythmia,
        first and second circuit boards comprising cardiac arrhythmia monitoring and therapy circuitry in electrical communication with the at least one capacitor, the first and second circuit boards being affixed to opposing sides of the impact-resistant energy core in a manner to allow for separation from the impact-resistant energy core during service, and
        an ingress-protective housing configured to enable removal of the impact-resistant energy core and the first and second circuit boards during service, wherein the ingress-protective housing comprises at least two shells configured to mate in a sealed configuration, the at least two shells configured to receive the impact-resistant energy core and the affixed first and second circuit boards therein, wherein one or more of the at least two shells comprises at least one shock absorbing spacer disposed therein, the at least one shock absorbing spacer positioned to support the impact-resistant energy core and the affixed first and second circuit boards within the ingress-protective housing such that, upon impact, the impact resistant energy core and the affixed first and second circuit boards deform into the at least one shock absorbing spacer and the first and second circuit boards are prevented from flexing, thereby protecting the impact-resistant energy core and the affixed first and second circuit boards from mechanical impact.

2. The device of claim 1, wherein the frame comprises a pocket configured to receive the at least one capacitor therein, the device comprising an insulating compound disposed within the pocket to at least partially encapsulate the at least one capacitor thereby immovably binding the at least one capacitor to the frame to form the unitary mass.

3. The device of claim 2, wherein the compound comprises an epoxy resin that when set after initial application has a hardness rating in a range of about 80-85 Shore D.

4. The device of claim 1, wherein the at least one capacitor comprises a film capacitor.

5. The device of claim 1, wherein the at least one capacitor comprises at least two capacitors.

6. The device of claim 1, further comprising at least one wire extending from the impact-resistant energy core.

7. The device of claim 6, wherein the at least one capacitor comprises two capacitors connected in parallel and the at least one wire is connected to the first circuit board.

8. The device of claim 7, wherein the two capacitors are two film capacitors arranged side-by-side each comprising two major planes such that the two major planes of each of the two film capacitors are disposed adjacent a first side and a second side of the frame.

9. The device of claim 1, wherein the at least one capacitor is configured to occupy at least 50 to 95 percent of a volume defined within a pocket in the frame.

10. The device of claim 1, further comprising one or more releasable fasteners configured to affix the first and second circuit boards to opposing sides of the impact-resistant energy core, the one or more releasable fasteners comprising one or more of screws, clamps, snaps, clips, or tape.

11. The device of claim 1, wherein the first circuit board comprises at least one processor and high voltage circuitry in communication with the at least one processor.

12. The device of claim 11, wherein the at least one processor comprises an arrhythmia detection processor.

13. The device of claim 11, wherein the at least one processor comprises an arrhythmia detection processor and a therapy control processor.

14. The device of claim 11, wherein the high voltage circuitry comprises a therapy delivery circuit.

15. The device of claim 1, further comprising a flex connector extending from the first circuit board to the second circuit board.

16. The device of claim 1, wherein the second circuit board comprises low voltage circuitry.

17. The device of claim 16, wherein the low voltage circuitry comprises communication circuitry.

18. The device of claim 1, wherein the first circuit board comprises a display mount configured to retain a display screen in wired communication with the second circuit board.

19. The device of claim 1, wherein the impact-resistant energy core and the affixed first and second circuit boards occupy between about 25%-90% of a volume defined by the ingress-protective housing.

20. The device of claim 1, wherein the at least two shells configured to mate in a sealed configuration comprise a rear shell configured to be disposed adjacent the second circuit board and a front shell configured to be disposed adjacent the first circuit board, the front shell mating with the rear shell in the sealed configuration.

21. The device of claim 20, wherein the ingress-protective housing comprises an IP67 rating as set forth in IEC 60529 Standard for Ingress Protection.

22. The device of claim 20, wherein the front shell comprises a touch screen disposed therein.

23. The device of claim 20, wherein the front shell comprises a speaker disposed therein.

24. The device of claim 20, further comprising a connector in communication with the plurality of ECG sensing and therapy electrodes, the connector configured to be mated to the ingress-protective housing in electrical communication with one or both of the first and second circuit boards, and the connector providing the separable electrical communication between the device controller and the plurality of ECG sensing and therapy electrodes in the garment.

25. The device of claim 24, wherein the ingress-protective housing further comprises a receiving port for the connector, the receiving port being in electrical communication with one or both of the first and second circuit boards.

26. The device of claim 20, wherein the rear shell further comprises a battery connector extending therethrough configured to receive a complimentary connector of a removable battery.

* * * * *